United States Patent
Sarma et al.

(10) Patent No.: US 12,364,267 B2
(45) Date of Patent: Jul. 22, 2025

(54) WHOLE CELL METHANOTROPH BASED BIOSTIMULANT COMPOSITIONS, METHODS AND APPLICATIONS THEREOF

(71) Applicant: STRING BIO PRIVATE LIMITED, Karnataka (IN)

(72) Inventors: Rajeev Kumar Sarma, Bangalore (IN); Uday Kashinath Avalakki, Bangalore (IN); Ravindra Babu Bondalakunta, Bangalore (IN); Prashanth Muralidhar Udagatti, Bangalore (IN); Vinod Munisanjeevaiah Lakshmi Kumar, Bangalore (IN); Ezhilkani Subbian, Bangalore (IN); Pavithra GJ, Bangalore (IN)

(73) Assignee: String Bio Private Limited, Bangalore (IN)

( * ) Notice: Subject to any disclaimer, the term of this patent is extended or adjusted under 35 U.S.C. 154(b) by 466 days.

(21) Appl. No.: 17/928,096

(22) PCT Filed: May 28, 2021

(86) PCT No.: PCT/IB2021/054712
§ 371 (c)(1),
(2) Date: Nov. 28, 2022

(87) PCT Pub. No.: WO2021/240472
PCT Pub. Date: Dec. 2, 2021

(65) Prior Publication Data
US 2023/0217929 A1    Jul. 13, 2023

(30) Foreign Application Priority Data
May 28, 2020 (IN) .............................. 202041022403

(51) Int. Cl.
*A01N 63/20*    (2020.01)
*A01P 21/00*    (2006.01)
*C12N 1/20*    (2006.01)

(52) U.S. Cl.
CPC .............. *A01N 63/20* (2020.01); *A01P 21/00* (2021.08); *C12N 1/205* (2021.05)

(58) Field of Classification Search
None
See application file for complete search history.

(56) References Cited

FOREIGN PATENT DOCUMENTS

| WO | 2017/195103 A1 | 11/2017 |
|----|----|----|
| WO | 2020/095281 A1 | 5/2020 |

OTHER PUBLICATIONS

Oct. 1, 2021 Search Report issued in International Application No. PCT/IB2021/054712.
Sukmawati, Dalla et al.; "The effectiveness of methanotrophic bacteria and Ochrobactrum anthropi to reduce CH4 and N2O emissions and to promote paddy growth in lowland paddy fields"; Malaysian Journal of Microbiology; vol. 12; No. 1; Mar. 2016; pp. 50-55.
Taopan, Rizki A. et al; "The Effect of Methanotrophic Bacteria Application on Paddy Growth and Methane Emission in Rainfed Rice of Kupang Regency East Nusa Tnggara, Indonesia"; International Journal of Environment, Agriculture and Biotechnology; vol. 3; No. 5; Jan. 2018; pp. 1759-1764.
Hadianta, Randi et al.: "Diversity of Nitrogen Fixing Bacteria Based on nifH Gene in Rice Fields"; Advances in Environmental Biology; vol. 8; No. 8; Jan. 2014; pp. 63-69.
Kumar, Manish et al.; "Methylotrophic bacteria in sustainable agriculture"; World Journal of Microbiology & Biotechnology; vol. 32; No. 7; Jun. 2016; pp. 1-9.
Oct. 1, 2021 Written Opinion of the International Searching Authority in International Patent Application No. PCT/IB2021/054712.
Whittenbury R. et al.; "Enrichment, Isolation and Some Properties of Methane-utilizing Bacteria"; Journal of General Microbiology; 1970; pp. 205-218.
American Type Culture Collection; "Methylococcus capsulatus Foster and Davis"; 2021; Product Sheet; pp. 1-6.

*Primary Examiner* — Alton N Pryor
(74) *Attorney, Agent, or Firm* — Oliff PLC

(57) ABSTRACT

Whole cell based biostimulant compositions and methods for improving agricultural productivity the compositions including: a microbial consortium having gammaproteobacterial methanotroph. As a result of these methanotrophs, the biostimulant composition enables plant performance improvement, utilization of methane, and facilitates improved nitrogen fixation in plants. The composition also helps in reducing the need of external chemical fertilizers for plant growth, development, performance and/or survival.

19 Claims, 10 Drawing Sheets

WHOLE CELL METHANOTROPH BASED BIOSTIMULANT COMPOSITIONS, METHODS AND APPLICATIONS THEREOF

TECHNICAL FIELD

The instant disclosure is in the field of biosciences, particularly focused towards biotechnology, agricultural science and environmental science. The disclosure particularly relates to whole cell based biostimulant compositions and methods for improving agricultural productivity. In particular, the compositions disclosed herein comprise a microbial consortium having gammaproteobacterial methanotroph. As a result of these methanotrophs, the biostimulant composition enables plant performance improvement, utilization of methane, and facilitates improved nitrogen fixation in plants. The composition also helps in reducing the need of external chemical fertilizers for plant growth, development, performance and/or survival.

BACKGROUND OF THE DISCLOSURE

Increasing agricultural production is an immediate need in today's world. The global population is projected to reach 9.6 billion by 2050. To meet the needs of the increasing population in coming years, agricultural production must be increased by about 60-70 percent from the current level, which is not going to be easy.

The growing scarcity of natural resources such as land, water and energy resources underline the fact that global agriculture will have to cope with the effects of climate change, extreme temperatures, unpredictable rainfall, and other stress factors. While the agricultural industries adapt to changing times, there are additional challenges and side-effects arising from increasing the agricultural productivity. For instance, world consumption of NPK-nitrogen (N), phosphorus expressed as phosphate ($P_2O_5$), and potassium expressed as potash ($K_2O$) was 292 million tonnes in 2016 and is expected to increase to 318 million tonnes by 2022. The demand for NPK is growing annually on average by 2.2% from 2015 to 2020. (FAO 2019; World fertilizer trends and outlook to 2022; Rome). This continued and increasing use of synthetic fertilizers however poses severe environmental threat. For instance, long term use of chemical fertilizer alters soil pH and microflora and leads to increase in pests and plant pathogens. This in turn negatively affects the beneficial microbial community in soil. Further, as chemical fertilizers are highly soluble in water, they leach out to ground water and pollute water table. Excess use of chemical fertilizers also depletes essential nutrients in soil. Food crops produced in such soil typically have less vitamin and mineral content. Thus, use of NPK and other such chemical fertilizers pose multiple side effects, and it is therefore a continuous challenge to address this issue. There is a hence a need to plug this excess use of chemical fertilizers.

However, one of the obstacles in doing so is to find alternate and efficient ways and means that help continually improve nitrogen availability/fixation in plants/crops so that the use of chemical fertilizers can be reduced to a significant level. While progress has been made in utilizing nitrogen fixing microorganisms to improve nitrogen availability/fixation in plants/crops, there is a continuous need for better approaches.

Another global concern today is environmental methane emissions which are one of the major contributors to climate change. Methane is a powerful greenhouse gas with 84 times the global warming potential compared to $CO_2$ over a 20 year period. While methane is generated in the course of several naturally occurring processes, it is its anthropogenic generation (resulting from human actions) that forms the majority of the methane emissions and is of concern. Agricultural activity is one such area of concern as it is responsible for a large share of anthropogenic methane emissions. Globally, agricultural activities contribute to about 40% of methane emissions (Agriculture and Climate Change, Mckinsey & Company, April 2020). While researchers across the globe are intensifying their focus on combating climate change, there is a dire need for reducing methane emitted during agricultural activities. More importantly, there is a greater need to utilize/channelize/recycle these agricultural methane emissions in an efficient, environment friendly and sustainable way.

Thus, there is an immense need to address some of the above important concerns/challenges, especially to reduce the levels of methane in atmosphere and improve agricultural productivity in an environment friendly and sustainable manner. The present disclosure addresses said need through a novel/unique approach.

SUMMARY

The present disclosure relates to a biostimulant composition comprising a microbial consortium of whole cells, wherein the consortium comprises at least 50% whole cells of gammaproteobacterial methanotroph.

In some embodiments, the composition further comprises at least one metabolite, at least one media derived nutrient and optionally at least one agriculturally acceptable excipient.

In some embodiments, the microbial consortium of whole cells comprises about $1 \times 10^3$ cells to about $5 \times 10^{10}$ cells per gram or per millilitre of the composition.

In some embodiments, the microbial consortium within the composition utilizes methane, and wherein the composition:
  a. improves or enhances performance of the plant,
  b. increases availability or efficient utilization of at least one of nitrogen, phosphorus and potassium by the plant,
  c. reduces the need for external addition of at least one nutrient selected from nitrogen, phosphorus and potassium, either individually or as part of a fertilizer, or
  d. any combination of a. to c.

The present disclosure accordingly also relates to a method of improving or enhancing plant performance, said method comprising contacting or applying the said biostimulant composition to a plant.

In some embodiments, the composition improves or enhances plant performance which comprises stimulating or promoting a quantitative or qualitative plant attribute selected from a group comprising biomass production, yield, photosynthetic activity, nutritional value, secondary metabolites and nutrient use efficiency, or any combination thereof.

Further, the present disclosure also relates to a method for facilitating simultaneous utilization of methane and nitrogen fixation in a plant, said method comprising contacting or applying the said biostimulant composition, to the plant.

In some embodiments, the nitrogen fixation is facilitated by increase in expression of genes of nitrogenase cluster selected from a group comprising nifA, nifD, nifH and nifK, or any combination thereof, in the microbial whole cells present in the biostimulant.

The present disclosure also relates to a method of reducing need of external addition of at least one nutrient or nutrient carrying fertilizer for growth, development, performance and/or survival of a plant, said method comprising contacting or applying the said biostimulant composition, to the plant.

In some embodiments, the nutrient is selected from a group comprising nitrogen, phosphorus and potassium, or any combination thereof.

In some embodiments, the composition improves or enhances the plant performance by either increasing availability of or efficient utilization of at least one of nitrogen, phosphorus and potassium by the plant, or both.

The present disclosure also provides a process of preparing the biostimulant composition, said method comprising combining a consortium comprising at least 50% whole cells of gammaproteobacterial methanotroph, with at least one of metabolite and media derived nutrient, optionally along with at least one agriculturally acceptable excipient.

In some embodiments, also provided are uses of the biostimulant composition herein.

DESCRIPTION

Figure 1:
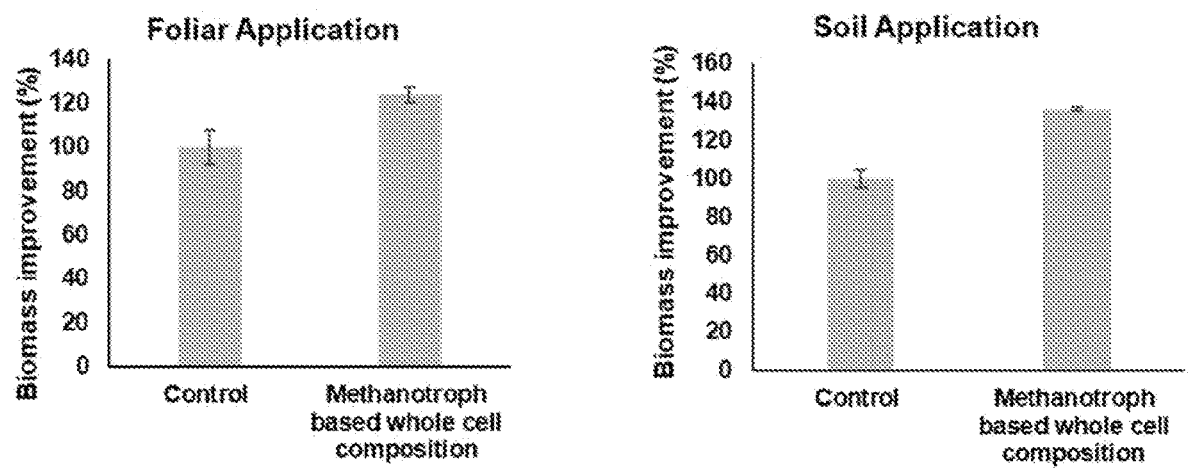
FIG. 1—Effect of methanotroph based whole cell composition on yield improvement in spinach. Foliar and soil application of methanotroph based whole cell composition resulted in 23-36% improvement in produce biomass.

In view of the limitations discussed above, and to remedy the need in the art for an efficient way of improving agricultural activity, along with reducing the levels of methane generated due to agricultural activities, the present disclosure provides a biostimulant composition that comprises a microbial consortium of whole cells, that not only improves or enhances performance of a plant but does so while reducing carbon footprint generated by methane.

Thus, the present disclosure aims at addressing the need for improving agricultural productivity in an environment friendly and sustainable approach using a technological solution.

More particularly, the present disclosure provides an efficient way to reduce the levels of methane in atmosphere and improve agricultural productivity in an environment friendly and sustainable manner, by providing a biostimulant that comprises whole cells of gammaproteobacterial methanotroph. This biostimulant when applied to a plant not only increases its performance, but because of the presence of gammaproteobacterial methanotroph, efficiently utilizes methane.

Accordingly, the present disclosure addresses the issue revolving around effective utilization of methane emissions generated by agricultural activity or from other sources. In other words, an objective of the present disclosure is to reduce the carbon footprint (total greenhouse gas emissions) caused by methane emitted during agricultural activity, and while doing so, make use of the same methane to provide for improved agricultural productivity.

One of the ways through which this objective of the present disclosure is achieved, is by making the plant more efficient in the manner in which it utilizes nutrients such as nitrogen, phosphorus and potassium, for its growth. Increasing nitrogen fixation is one such example, that allows higher availability of nitrogen to the plant. Thus, another objective of the present disclosure is to improve nitrogen fixation in plants and/or, increase the nitrogen availability to the plants.

Combining this aspect of increased nitrogen fixation with better methane utilization therefore forms another objective of the present disclosure. The aim is to facilitate methane utilization and nitrogen fixation in an environment friendly/biological manner. Particularly, an objective is to facilitate simultaneous atmospheric methane utilization and nitrogen availability/fixation in an environment friendly/biological manner, as a means for improving agricultural productivity.

Another way through which more efficient agricultural production is achieved is by reducing the amounts of chemical/synthetic fertilizers that are employed for growth of a plant. Typically, such fertilizers cause adverse effect to the soil, environment and the water table, thereby impacting the overall ecosystem. Providing a biostimulant that reduces a plant's dependence on chemical/synthetic fertilizers, is an example of innovative solution to this issue. Thus, another objective of the present disclosure is to reduce the use/application of chemical/synthetic fertilizers-based inputs, for agricultural activity.

Combining this aspect of reduced fertilizer use, with better methane utilization and nutrient absorption/nitrogen fixation is another objective of the present disclosure. The aim is to facilitate methane utilization, more efficient nutrient use, better nitrogen availability/fixation and reduce the use of chemical fertilizers in an environment friendly/biological manner. Particularly, an objective is to facilitate simultaneous methane utilization, nitrogen fixation and reduced use of chemical fertilizers in an environment friendly/biological manner, as a means for improving agricultural productivity.

The present disclosure thus aims at providing a simple, economical and sustainable solution for simultaneously addressing the aforesaid needs of: a) methane utilization arising due to methane emissions from agricultural activity or other sources, b) improved nutrient availability/nitrogen fixation in plants, c) reduced use of chemical fertilizers, and d) providing products and methods for improving agricultural productivity.

Before going into greater detail, provided below are definitions of some terms used throughout the present disclosure.

As used in the present disclosure, the term 'methanotroph(s)' or 'methanotroph' or 'methanotrophs' refer to prokaryotic cell that use methane as their primary and sole source of carbon and energy. In some embodiments of the present disclosure, methanotrophs employ methane as the sole source of carbon and energy. In some embodiments of the present disclosure, methanotrophs comprise methanotrophic bacteria.

As used in the present disclosure, the term 'gammaproteobacterial methanotroph' refers to methanotrophs that belong to the class of Gammaproteobacteria. These comprise of type I/type X methanotrophs. In some embodiments of the present disclosure, gammaproteobacterial methanotrophs include members of the family Methylococcaceae. An example of one such gammaproteobacterial methanotroph is *Methylococcus capsulatus* (also referred to herein as *M. capsulatus*).

As used in the present disclosure, the terms/phrases 'improving plant performance', 'enhancing plant performance', 'promoting plant growth' and the likes refer to stimulating/promoting one or more plant attributes important for plant growth, development, performance and/or survival, selected from but not limited to biomass production, yield, photosynthetic activity, nutritional value, secondary metabolites and nutrient use efficiency, or any combination thereof. The improvement or enhancement of the plant performance or plant growth comprises having a stimulating/promoting effect on plant as measured by outcomes selected from but not limited to—increase in number, size or quality of below ground or aerial biomass selected from a group comprising root, shoot, leaf, flowers, anthers, stigma, stamens, fruits and seeds or any combination thereof, increase in photosynthetic activity or chlorophyll content, increase in protein, dietary fibre, β-carotene or essential oil content, plant specific metabolites or any combination thereof, or efficient absorption or utilization of available or externally provided nutrients or minerals.

As used in the present disclosure, the terms 'increase', 'increased', 'increasing', 'enhance', 'enhanced', 'enhancing', 'promote', 'promoted', 'promoting', 'improve', 'improved', or 'improving' or their commonly known synonyms, are used interchangeably and refer to their usual meaning known in the art. In the context of the attributes with respect to plant growth, development, performance and/or survival, these terms are used herein to emphasize on the positive effect that the composition(s) or method(s) of the present disclosure has on the plant, that causes the plant to grow or survive better, when compared to its previous setting without use of the composition(s) or method(s) of the present disclosure.

As used in the present disclosure, the term 'metabolite' refers to an intermediate, precursor or end product of metabolism. In embodiments of the present disclosure, the metabolite includes products produced during metabolic reaction(s) in methanotroph(s). In some embodiments of the present disclosure, the metabolite includes products produced due to metabolic reaction(s) in methanotrophic bacteria during culturing of said methanotrophic bacteria.

As used in the present disclosure, the term 'cells', or 'whole cells' can be used interchangeably and refers to the collection or mass of microorganisms. In some embodiments of the present disclosure, the cells refer to the collection of methanotrophic bacterial cells. In some embodiments of the present disclosure, the cells refer to the collection of methanotrophic bacterial cells alone or in combination with plant growth-promoting microorganism(s).

As used in the present disclosure, the term 'microbial consortium', 'bacterial consortium' or 'consortium of microorganisms' or just 'consortium', all used interchangeably in the present disclosure, comprises one or more microorganisms functioning symbiotically or independently, wherein at least one of the microorganisms is a methanotroph. In some embodiments of the present disclosure, the microbial consortium comprises a combination of one or more species of microorganisms functioning symbiotically or independently, wherein at least one of the microorganisms is a methanotroph. In other embodiments of the present disclosure, the microbial consortium comprises a combination of at least one methanotrophic bacterium and at least one plant growth-promoting microorganism. In the context of the present disclosure, plant growth-promoting microorganism comprises nitrogen solubilizing microorganisms, phosphate solubilizing microorganism, mineral solubilizing microorganism, phytohormone secreting microorganism, organic acids secreting bacteria and plant beneficial microbe, or any combination thereof. In the context of the present disclosure, theses terms emphasize on the fact that at the least, the consortium comprises one or more gammaproteobacterial methanotroph, and thus a consortium can be completely made up of only gammaproteobacterial methanotrophs.

As used in the present disclosure, the term 'optionally', 'optional' and the likes mean that said component or feature may or may not be present as a part of the composition(s) or method(s) of the disclosure.

As used in the present disclosure, the term 'plant', 'crop' and the likes are used interchangeably and refer to plants under kingdom Plantae in general. In a preferred embodiment, the plants are agricultural plants, horticultural plants, cereal crops, cash crops, indoor plants, floriculture plants, plantation crops, spice crops, and combinations thereof.

As used in the present disclosure, the terms 'whole cell composition', 'methanotroph based whole cell composition', 'methanotroph based composition', 'methanotroph based product', 'biostimulant', 'biostimulant composition', 'whole cell biostimulant composition', 'plant biostimulant composition', 'plant biostimulant composition comprising whole cell methanotroph' and the likes are used interchangeably and refer to the product(s) of the present disclosure. Thus, the term biostimulant with or without any other accompanying term is meant to provide the same meaning, which is ordinarily known to a person skilled in the art, for example that of a biological or biologically derived composition that is used in plants to enhance their characteristics, productivity or efficiency. Similarly, it also encompasses compositions that include microorganisms which when applied to plants, seeds or the rhizosphere stimulate natural processes to benefit nutrient uptake, nutrient use efficiency, and/or crop quality, independently of its nutrient content. Particularly in the context of the present disclosure, the term biostimulant means any composition that comprises at least one microorganism, and is useful for a plant and provides at least one benefit that impacts the overall characteristics, productivity or efficiency of the plant.

As used in the present disclosure, the term 'nitrogen availability' or 'nitrogen fixation' and the likes is intended to refer to the general meaning of the terms known in the art. In the context of the present disclosure, it includes increasing the availability of nitrogen or enabling better utilization of nitrogen by the plants in the form of ammonia, nitrate, nitrite, protein, amino acids, peptides, nucleic acids through compositions such as the whole cell biostimulant composition described herein, either alone or in combination with other nitrogen fixing microorganisms and/or from other sources such as amino acids, glutamine, ammonium, urea, sulphur coated urea, methylene urea, polymer coated urea, isobutylidene diurea, nitrate, nitrite, ammonium containing molecules, nitrate containing molecules or nitrite containing molecules or any combinations thereof.

As used in the present disclosure, the term 'phosphorous availability' and the likes is intended to refer to the general meaning of the term known in the art. In the context of the present disclosure, it includes increasing the availability or enabling better utilization of phosphorous to the plants through compositions such as the whole cell methanotroph composition described herein, either alone or in combination with other phosphate solubilizing microorganisms and/or from sources comprising diammonium phosphate, monoammonium phosphate, single super phosphate, ammonium dihydrogen phosphate, ammonium phosphate, super phosphate, tricalcium phosphate or any combinations thereof as a source of phosphate.

As used in the present disclosure, the term 'potassium availability' and the likes is intended to refer to the general meaning of the terms known in the art. In the context of the present disclosure, it includes increasing the availability or enabling better utilization of potassium to the plants in the form of potassium from compositions such as the whole cell methanotroph composition described herein, either alone or in combination with other potassium solubilizing microorganisms and/or from sources comprising but not limited to muriate of potash, sulphate of potash, potassium nitrate, sulfate potash magnesia, kainite or any combinations thereof as a source of potassium.

Accordingly, to reiterate, the present disclosure provides for a biostimulant composition comprising gammaproteobacterial methanotroph. When applied to a plant, the biostimulant composition improves or enhances performance of the plant. Furthermore, since the composition comprises gammaproteobacterial methanotrophs, a method for facilitating simultaneous utilization of methane and nitrogen fixation in a plant is also provided, said method comprising contacting or applying the biostimulant composition to the plant. Consequently, the biostimulant composition improves the overall efficiency of the plant, and therefore allows for reduction in external addition of at least one nutrient or nutrient carrying fertilizer for growth, development, performance and/or survival of the plant.

The composition(s), their use and associated method(s) of the present disclosure are further described in greater detail in the following embodiments. For the sake of brevity, identical embodiments may not be repeated for each of the different composition(s), use(s) or method(s) described herein. However, any combination of an embodiment captured anywhere in this disclosure with any other embodiment captured elsewhere in this disclosure, fall wholly within the ambit of the present disclosure. Such combinations can therefore be taken into account to derive complete meaning of the aspects described herein.

Biostimulant Composition

The present disclosure provides a biostimulant composition based on a microbial consortium that includes methanotrophs, preferably methanotrophic bacteria, for improving plant performance, methane utilization and nitrogen fixation/availability in plants. The composition also allows for reduction in use of chemical or synthetic fertilizers normally used in the course of agricultural activities.

As mentioned previously, since one of the objectives of the present disclosure is to improve or enhance plant performance while utilizing a greenhouse gas as methane, it is important that a corresponding composition includes microorganisms that can efficiently use methane generated by agricultural activities and other sources, and uses it to provide benefits for a plant. This is achieved by the presence of microbial consortium that includes gammaproteobacterial methanotroph, in the compositions of the present disclosure.

This gammaproteobacterial methanotroph is present in a consortium that comprises a total of about $1 \times 10^3$ whole cells to about $5 \times 10^{10}$ whole cells per gram or per millilitre of the compositions of the present disclosure, and includes all values and ranges therein.

In some embodiments, the microbial consortium comprises a total of about $5 \times 10^3$ whole cells to about $5 \times 10^{10}$ whole cells, and includes all values and ranges therein. In other embodiments, the microbial consortium comprises a total of about $1 \times 10^3$ whole cells to about $1 \times 10^{10}$ whole cells, and includes all values and ranges therein.

In some embodiments, a gammaproteobacterial methanotroph is a microorganism capable of using methane as the primary source or the sole source of carbon and/or energy.

Thus, the present disclosure provides a biostimulant composition comprising a microbial consortium of whole cells, that includes whole cells of gammaproteobacterial methanotroph.

Since these gammaproteobacterial methanotrophs are known to efficiently utilize methane for their growth and survival, the composition of the present disclosure employs them to not only utilize methane but to do so while providing beneficial effect to the plant that the composition is applied to. Accordingly, the gammaproteobacterial methanotroph form the most important part of the composition of the present disclosure. They therefore form the majority of the microorganisms that are present in the composition.

Accordingly, the present disclosure provides a biostimulant composition comprising a microbial consortium of whole cells, wherein the consortium comprises at least 50% whole cells of gammaproteobacterial methanotroph.

In some embodiments, the microbial consortium within the biostimulant composition comprises at least about 60% to about 100% whole cells of gammaproteobacterial methanotroph, and includes all values and ranges therein.

In some embodiments, the microbial consortium within the composition comprises at least about 60% whole cells of gammaproteobacterial methanotroph.

In some embodiments, the microbial consortium within the composition comprises at least about 70% whole cells of gammaproteobacterial methanotroph.

In some embodiments, the microbial consortium within the composition comprises at least about 80% whole cells of gammaproteobacterial methanotroph.

In some embodiments, the microbial consortium within the composition comprises at least about 90% whole cells of gammaproteobacterial methanotroph.

In some embodiments, the microbial consortium within the composition comprises at least about 99% whole cells of gammaproteobacterial methanotroph.

Accordingly, in some embodiments, the microbial consortium within the composition essentially consists of whole cells of gammaproteobacterial methanotroph.

In some embodiments, the microbial consortium within the composition consists of whole cells of gammaproteobacterial methanotroph.

In some embodiments, the gammaproteobacterial methanotroph employed in the biostimulant composition is a type I or type X methanotroph belonging to genus selected from a group comprising *Methylococcus, Methylomonas, Methylobacter, Methyloglobulus, Methylovulum, Methylomicrobium, Methylosarcina, Methylosphaera, Methyloprofundus, Methylosoma, Methylocucumis, Methylocaldum, Methyloparacoccus, Methylogaea, Methylomagnum, Methyloterricola, Methylothermus, Methylohalobius, Methylomarinovum, Methylomarinum* and *Crenothrix*, or any combination thereof.

In some embodiments, the gammaproteobacterial methanotroph employed in the biostimulant composition is a type I or type X methanotroph is selected from a group comprising *Methylococcus* sp., *Methylomonas* sp., *Methylobacter* sp., *Methyloglobulus* sp., *Methylovulum* sp., *Methylomicrobium* sp., *Methylosarcina* sp., *Methylosphaera* sp., *Methyloprofundus* sp., *Methylosoma* sp., *Methylocucumis* sp., *Methylocaldum* sp., *Methyloparacoccus* sp., *Methylogaea* sp., *Methylomagnum* sp., *Methyloterricola* sp., *Methylothermus* sp., *Methylohalobius* sp., *Methylomarinum* sp., *Methylomarinovum* sp. and *Crenothrix* sp., *or any combination thereof.*

In some embodiments, the gammaproteobacterial methanotroph is selected from a group comprising *Methylococcus capsulatus, Methylococcus mobilis, Methylomicrobium kenyense, Methylomicrobium alcaliphilum, Methylomicrobium alcaliphilum 20Z, Methylomicrobium buryatense 5G, Methylomicrobium buryatense 4G, Halomonas pantelleriensis, Methylomicrobium album, Methylomonas methanica*, MB 126, *Methylobacter tundripaludum, Methylovulum miyakonense, Methylomonas rubra, Methylomonas koyamae, Methylomonas methancia, Methylomonas denitrificans, Methylomonas paludis, Methylomonas lenta, Methylomarinum vadi, Methylococcus thermophilus, Methylobacter whittenburyi, Crenothrix polyspora, Clonothrix fusca, Methylobacter bovis, Methylomonas aurantiaca, Methylomonas fodinarum, Methylobacter vinelandii, Methylomicrobium japanense, Methylococcaceae bacterium, Methylocystis methanolicus, Methylocucumis oryzae, Methylogaea oryzae, Methylosarcina lacus, Methylosoma difficile* and combinations thereof.

In some embodiments of the composition, the gammaproteobacterial methanotroph is selected from a group comprising *Methylococcus capsulatus, Methylocucumis oryzae, Methylogaea oryzae, Methylomicrobium alcaliphilum, Methylomicrobium alcaliphilum 20Z, Methylomicrobium buryatense 5G, Methylomicrobium buryatense 4G, Halomonas pantelleriensis, Methylobacter tundripaludum, Methylobacter whittenburyi, Methylobacter marinus, Methylobacter luteus Methylosarcina lacus, Methylosarcina fibrata, Methylotericola oryzae, Methylosoma difficile, Methylomonas methanica, Methylomonas denitrificans, Methylomonas koyamae, Methylomicrobium album, Methylomicrobium agile, Methylovulum miyakonense, Methylovulum psychorotolerans, Methylomagnum ishizawai Methylohalobius crimeensis, Crenothrix polyspora, Methyloprofundus sedimenti*, and combinations thereof.

In some embodiments, the microbial consortium comprises a total of about $1\times10^3$ whole cells to about $5\times10^{10}$ whole cells per gram or per millilitre of the composition, and includes all values and ranges therein. As mentioned, out of these total cells, at least 50% whole cells are of gammaproteobacterial methanotrophs.

In some embodiments, the gammaproteobacterial methanotroph employed in the biostimulant composition is *Methylococcus capsulatus*.

Thus, in some embodiments, the microbial consortium within the biostimulant composition comprises at least about 60% to about 100% whole cells of *Methylococcus capsulatus*, and includes all values and ranges therein.

In some embodiments, the microbial consortium within the composition comprises at least about 60% whole cells of *Methylococcus capsulatus*.

In some embodiments, the microbial consortium within the composition comprises at least about 70% whole cells of *Methylococcus capsulatus*.

In some embodiments, the microbial consortium within the composition comprises at least about 80% whole cells of *Methylococcus capsulatus*.

In some embodiments, the microbial consortium within the composition comprises at least about 90% whole cells of *Methylococcus capsulatus*.

In some embodiments, the microbial consortium within the composition comprises at least about 99% whole cells of *Methylococcus capsulatus*.

In some embodiments, the microbial consortium within the composition essentially consists of whole cells of *Methylococcus capsulatus*.

In some embodiments, the microbial consortium within the composition consists of whole cells of *Methylococcus capsulatus*.

In some embodiments, the microbial consortium comprises a total of about $1\times10^3$ whole cells to about $5\times10^{10}$ whole cells of *Methylococcus capsulatus* per gram or per millilitre of the composition, and includes all values and ranges therein.

In some embodiments, the microbial consortium comprises a total of about $5\times10^3$ whole cells to about $5\times10^{10}$ whole cells of *Methylococcus capsulatus* per gram or per millilitre of the composition.

In some embodiments, the microbial consortium comprises a total of about $1\times10^3$ whole cells to about $1\times10^{10}$ whole cells of *Methylococcus capsulatus* per gram or per millilitre of the composition.

In some embodiments, the microbial consortium comprises at least about $0.5\times10^3$ whole cells to about $2.5\times10^{10}$ whole cells of *Methylococcus capsulatus* per gram or per millilitre of the composition.

In some embodiments, the microbial consortium comprises at least about $1\times10^5$ whole cells to about $1\times10^8$ whole cells of *Methylococcus capsulatus* per gram or per millilitre of the composition.

In some embodiments, apart from the gammaproteobacterial methanotroph, the microbial consortium comprises other plant growth-promoting microbes/microorganisms (PGPM) selected from a group comprising but not limited to nitrogen fixing microorganism, phosphate solubilizing microorganism, mineral solubilizing microorganism, phytohormone secreting microorganism, organic acids secreting bacteria, other plant beneficial microbes and combinations thereof. The PGPM accordingly comprises about 10% to about 50% the consortium.

Thus, in some embodiments, the microbial consortium comprises at least 50% whole cells of gammaproteobacterial methanotroph, along with other plant growth-promoting microorganisms selected from a group comprising but not limited to nitrogen fixing microorganism, phosphate solubilizing microorganism, mineral solubilizing microorganism, phytohormone secreting microorganism, organic acids secreting bacteria, other plant beneficial microbes and combinations thereof.

Accordingly, in some embodiments, the microbial consortium comprises *Methylococcus capsulatus*, along with other plant growth-promoting microorganisms selected from a group comprising but not limited to nitrogen fixing microorganism, phosphate solubilizing microorganism, mineral solubilizing microorganism, phytohormone secreting microorganism, organic acids secreting bacteria, other plant beneficial microbes and combinations thereof.

Thus, in some embodiments, the microbial consortium comprises at least 50% whole cells of *Methylococcus capsulatus*, along with other plant growth-promoting microorganisms selected from a group comprising but not limited to nitrogen fixing microorganism, phosphate solubilizing microorganism, mineral solubilizing microorganism, phytohormone secreting microorganism, organic acids secreting bacteria, other plant beneficial microbes and combinations thereof.

In some embodiments, the plant growth-promoting microbe is a plant growth-promoting bacteria (PGPB), endophytic bacteria, endophytic fungi, epiphytic bacteria, epiphytic fungi, mycorrhizal fungi, vesicular-arbuscular mycorrhiza (VAM), or any combinations thereof.

In some embodiments, the plant growth-promoting bacteria (PGPB) is plant growth-promoting rhizobacteria (PGPR).

Thus, in some embodiments, the microbial consortium of the present disclosure comprises primarily of gammaproteobacterial methanotrophs, such as *M. capsulatus*.

In some embodiments, the microbial consortium of the present disclosure comprises of gammaproteobacterial methanotrophs, such as *M. capsulatus* and one or more PGPMs in a ratio of about 90:10.

In some embodiments, the microbial consortium of the present disclosure comprises of gammaproteobacterial methanotrophs, such as *M. capsulatus* and one or more PGPMs in a ratio of about 80:20.

In some embodiments, the microbial consortium of the present disclosure comprises of gammaproteobacterial methanotrophs, such as *M. capsulatus* and one or more PGPMs in a ratio of about 70:30.

In some embodiments, the microbial consortium of the present disclosure comprises of gammaproteobacterial methanotrophs, such as *M. capsulatus* and one or more PGPMs in a ratio of about 60:40.

In some embodiments, the microbial consortium of the present disclosure comprises of gammaproteobacterial methanotrophs, such as *M. capsulatus* and one or more PGPMs in a ratio of about 50:50.

Apart from the microbial consortium comprising the whole cells of gammaproteobacterial methanotroph, such as *M. capsulatus*, the biostimulant composition also comprises at least one metabolite, at least one media derived nutrient and optionally at least one agriculturally acceptable excipient.

The present disclosure therefore provides a biostimulant composition comprising a microbial consortium having gammaproteobacterial methanotroph, such as *M. capsulatus*, at least one metabolite, at least one media derived nutrient and optionally at least one agriculturally acceptable excipient.

In some embodiments, the biostimulant composition comprises a microbial consortium having *Methylococcus capsulatus*, at least one metabolite, at least one media derived nutrient and optionally at least one agriculturally acceptable excipient.

In some embodiments, the biostimulant composition comprises a microbial consortium having *Methylococcus capsulatus*, at least one metabolite, at least one media derived nutrients and at least one agriculturally acceptable excipient.

In some embodiments, the biostimulant composition comprises a microbial consortium having at least one methanotroph and at least one plant growth-promoting microbe (PGPM), at least one metabolite, at least one media derived nutrient and optionally at least one agriculturally acceptable excipient.

In all embodiments of the biostimulant composition of the present disclosure, the microbial consortium of whole cells comprises a total of about $1\times10^3$ cells to about $5\times10^{10}$ cells per gram or per millilitre of the composition, and includes all values and ranges therein.

In some embodiments, the said consortium of total of $1\times10^3$ cells to about $5\times10^{10}$ cells per gram or per millilitre of the composition constitutes about 0.1% to about 80% of the biostimulant composition of the present disclosure. The remainder of the composition is constituted by about 0.10% to about 10% of at least one metabolite, about 0.1% to about 10% of at least one media derived nutrient and optionally about 0.01% to about 90% of at least one agriculturally acceptable excipient. The ranges mentioned above explicitly encompass all values and ranges therein.

In some embodiments, the metabolite comprises a component derived from culture broth. In some embodiments, the metabolite comprises a component derived from culture broth, wherein said culture broth is obtained by culturing a methanotroph. In particular, the metabolite comprises a component produced by the gammaproteobacterial methanotrophic cells as a result of culturing them in a culture media.

In some embodiments, the metabolite comprises a component selected from a group comprising but not limited to carbohydrates, lipids, sugars, fatty acids, proteins, peptides, nucleic acids, nucleotides, amino acids, vitamins, organic acids, salts, minerals, extracellular enzymes, osmolytes, bacterial derived components, minerals and combinations thereof.

In some embodiments, the metabolite comprises a component selected from a group comprising peptide or a mixture of peptides, free amino acids, nucleic acids, nucleotides, vitamins, carbohydrates, lipids, sugars, fatty acids, salts, minerals, osmolytes, extracellular enzymes, bacterial derived components, ash and combinations thereof.

In some embodiments, the media derived nutrient comprises a component derived from culture media.

In some embodiments, the media derived nutrient comprises a component derived from culture media employed for culturing a methanotroph, more particularly a gammaproteobacterial methanotroph. Accordingly, the media derived nutrient comprises a component not produced by the methanotrophic cells and rather added as a part of the culture media during culturing of the methanotrophic cells. In a specific embodiment, the media derived nutrient is a component in the culture media used to grow methanotroph. In some embodiments, the term 'media derived nutrient' and 'non-cellular nutrient' are employed interchangeably and mean the same.

In some embodiments, the media derived nutrient comprises an inorganic nutrient.

In some embodiments, the media derived nutrient comprises a mineral.

In some embodiments, the media derived nutrient comprises ions, salts, or a combination thereof.

In some embodiments, the ions are cations, anions, or a combination thereof.

In some embodiments, the cations are selected from a group comprising sodium, potassium, magnesium, manganese, cobalt, zinc, copper, iron, calcium, boron, nickel, molybdenum, calcium and combinations thereof.

In some embodiments, the anions are selected from a group comprising sulphates, chlorides, nitrates, phosphates, borates and combinations thereof.

In some embodiments, the media derived nutrient comprises salts selected from a group comprising sodium salt, potassium salt, magnesium salt, manganese salt, cobalt salt, zinc salt, copper salt, iron salt, calcium salt, boron salt, nickel salt and combinations thereof.

In some embodiments, the media derived nutrient comprises salts selected from a group comprising sodium chloride, potassium nitrate, magnesium sulphate, calcium chloride, sodium molybdate, ferrous sulphate, zinc sulphate, cobalt chloride, boric acid salt, zinc chloride, manganese chloride, nickel chloride, copper sulphate, phosphates of sodium/potassium and combinations thereof.

In some embodiments, the media derived nutrient comprises chelated salts wherein the salts are attached to a chelating agent.

In some embodiments, the chelating agent is selected from a group comprising ethylenediaminetetraacetic acid (EDTA), citric acid, hydroxyamino-polycarboxylic acid, diethylenetriamine pentaacetic acid, hydroxy ethylenediaminetriacetic acid, tetrakis hydroxymethyl phosphonium sulfate, nitrilotriacetic acid, and glutamic acid-diacetic acid, and combinations thereof.

In some embodiments, the media derived nutrient comprises a component selected from a group comprising sodium, potassium, magnesium, manganese, cobalt, zinc, copper, iron, calcium, molybdenum, boron, nickel, sulphate, chloride, nitrate, phosphates, borates, salts, chelated salts and combinations thereof.

In some embodiments, the agriculturally acceptable excipient comprises a component selected from a group comprising carrier, cell protectant, adjuvant, surfactant, stabilizer, preservative, diluent, suspending agent, dispersing agent, cosolvent and combinations thereof.

In some embodiments, the carrier is selected from group comprising but not limited to lignite, bentonite, peat, vermiculite, charcoal, soil mixture, farm yard manure and combinations thereof.

In some embodiments, the cell protectant is selected from a group comprising but not limited to polyethylene glycol (PEG), polyvinyl alcohol, sodium alginate, gelatin, gellan, welan and combinations thereof.

In some embodiments, the adjuvant is selected from a group comprising but not limited to xanthan gum, carboxymethyl cellulose (CMC), gum arabic, polyvinylpyrrolidone (PVP) and combinations thereof.

In some embodiments, the surfactant is selected from a group comprising but not limited to a cationic surfactant, anionic surfactant, non-ionic surfactant, silicon-based surfactant and combinations thereof.

In some embodiments, the surfactant is selected from a group comprising but not limited to a natural surfactant, semi-synthetic surfactant, synthetic surfactant and combinations thereof.

In some embodiments, the surfactant is selected from a group comprising but not limited to polyethylene glycol (PEG), polyvinylpyrrolidone (PVP), gum arabic, sodium alginate, Silwet L-77, Tween 20, Tween 80, Triton X 100 and combinations thereof.

In some embodiments, the stabilizer or preservative is selected from a group comprising but not limited to potassium sorbate, sorbic acid, trehalose, citric acid, polyglutamic acid and combinations thereof.

In some embodiments, the diluent is selected from a group comprising ionic buffer-based diluent solution, saline solution and a combination thereof.

Accordingly, in some embodiments, the biostimulant composition comprises a microbial consortium having at least 50% whole cells of gammaproteobacterial methanotroph, the metabolite comprising one or more components: carbohydrates, sugars, lipids, fatty acids, proteins, amino acids, peptides, organic acids, nucleic acids, nucleotides, vitamins, other cellular metabolites, minerals and osmolytes, and the non-cellular nutrient comprising one or more components: minerals, salts, ions; and optionally one or more agriculturally acceptable excipient.

In some embodiments, the biostimulant composition comprises a microbial consortium having at least 50% whole cells of gammaproteobacterial methanotroph, the metabolite comprising one or more components: carbohydrates, sugars, lipids, fatty acids, proteins, amino acids, peptides, organic acids, nucleic acids, nucleotides, vitamins, other cellular metabolites, minerals and osmolytes, and the non-cellular nutrient comprising one or more components: sulphates, phosphates, chlorides, nitrates, sodium, potassium, magnesium, manganese, calcium, copper, cobalt, molybdenum, zinc, nickel and iron; and optionally one or more agriculturally acceptable excipient.

In some embodiments, the biostimulant composition comprises a microbial consortium having at least 50% whole cells of *Methylococcus capsulatus*; metabolite comprising one or more components: carbohydrates, sugars, fatty acids, lipids, proteins, peptides, amino acids, vitamins, organic acids, and osmolytes; media nutrient comprising one or more components: minerals, salts and ions; and optionally one or more agriculturally acceptable excipient.

In some embodiments, the biostimulant composition comprises a microbial consortium having at least 50% whole cells of *Methylococcus capsulatus*; metabolite comprising one or more components: carbohydrates, sugars, fatty acids, lipids, proteins, peptides, amino acids, vitamins, organic acids and osmolytes; media derived nutrient comprising one or more components: sulphates, phosphates, chlorides, nitrates, sodium, potassium, magnesium, calcium, copper, cobalt, molybdenum, zinc, nickel, iron; and optionally one or more agriculturally acceptable excipient.

In some embodiments, the biostimulant composition is in a liquid form or a solid form.

In some embodiments, the biostimulant composition is in a liquid form or a solid form, selected from but not limited to liquid sprays, dust, granular, beads, soluble powder, wettable powder, pellet, microencapsulated, emulsifiable concentrate, capsular suspension, dry flowable form, liquid Flowable, and the likes. While these forms provide examples of different ways in which the biostimulant composition of the present disclosure can be formulated, the activity of the composition is not dependent on or changes with the change in form. Hence, a person skilled in the art can employ the composition of the present disclosure in a form that suits their purpose the best.

Accordingly, in some embodiments, the microbial consortium comprises a total of about $1 \times 10^3$ whole cells to about $5 \times 10^{10}$ whole cells per gram of the solid composition or per millilitre of the liquid composition.

In some embodiments, the microbial consortium comprises a total of about $1 \times 10^3$ whole cells to about $5 \times 10^{10}$ whole cells per gram of the solid composition or per millilitre of the liquid composition, wherein at least 50% of the whole cells are of gammaproteobacterial methanotroph.

In some embodiments, the microbial consortium comprises a total of about $1 \times 10^3$ whole cells to about $5 \times 10^{10}$ whole cells of gammaproteobacterial methanotroph, such as *M. capsulatus*, per gram of the solid composition or per millilitre of the liquid composition, and includes all values and ranges therein.

In some embodiments, the biostimulant composition comprises whole cells at a concentration ranging from $1 \times 10^3$ cells/g to $5 \times 10^{10}$ cells/g in solid form composition or $1 \times 10^3$ cells/ml to $5 \times 10^{10}$ cells/ml in liquid form composition, the metabolite at a concentration ranging from about 0.10% to about 10% and the media derived nutrient at a concentration ranging from about 0.1% to about 10%. In any case, at least 50% of the whole cells within the microbial consortium of the composition are that of gammaproteobacterial methanotroph, such as *M. capsulatus*.

In some embodiments, the biostimulant composition comprises whole cells at a concentration ranging from $1 \times 10^3$ cells/g to $5 \times 10^{10}$ cells/g in solid form composition or $1 \times 10^3$ cells/ml to $5 \times 10^{10}$ cells/ml in liquid form composition, the metabolite at a concentration ranging from about 0.1% to about 10%, the media derived nutrient at a concentration ranging from about 0.1% to about 10% and the agriculturally acceptable excipient at a concentration ranging from about 0.01% to about 90%. In any case, at least 50% of the whole cells within the microbial consortium of the composition are that of gammaproteobacterial methanotroph, such as *M. capsulatus*.

In an exemplary embodiment, the metabolite in the composition comprises about 70% proteins, about 15% carbohydrates, about 7% lipids and about 8% minerals in the solid form.

In an exemplary embodiment, the metabolite in the composition comprises about 15% proteins, 5% carbohydrates, 3% lipids and about 3% minerals in the liquid form.

As described previously, in some embodiments, apart from the gammaproteobacterial methanotroph, such as *M. capsulatus*, the biostimulant composition further comprises a plant growth-promoting microorganism. Accordingly, in some embodiments, the consortium comprises about 1% to about 50% of at least one plant growth-promoting microbe.

Accordingly, in some embodiments, the composition comprises:
a microbial consortium comprising one or more gammaproteobacterial methanotrophic bacteria and one or more plant growth-promoting microbe (PGPM),
at least one metabolite,
at least one media derived nutrient, and
optionally, at least one agriculturally acceptable excipient.

In some embodiments, the methanotrophic bacteria, the metabolite, the non-cellular nutrient, the agriculturally acceptable excipient, and the plant growth-promoting microbe (PGPM) are as defined above.

In some embodiments, the composition comprises:
a microbial consortium comprising at least 50% whole cells of gammaproteobacterial methanotroph, such as *M. capsulatus*, and one or more plant growth-promoting microbe (PGPM), at a total whole cell concentration ranging from about $1 \times 10^3$ cells/g to $5 \times 10^{10}$ cells/g of solid composition or $1 \times 10^3$ cells/ml to $5 \times 10^{10}$ cells/ml of liquid composition,
metabolite(s) at a concentration ranging from about 0.1% to 10%,
media derived nutrient(s) at a concentration ranging from about 0.1% to 10%, and
optionally an agriculturally acceptable excipient at a concentration ranging from about 0.01% to 90%.

In some embodiments, the composition comprises:
a microbial consortium comprising at least 50% whole cells of gammaproteobacterial methanotroph, such as *M. capsulatus*, and one or more plant growth-promoting microbe (PGPM), at a total whole cell concentration ranging from about $1 \times 10^3$ cells/g to $5 \times 10^{10}$ cells/g of solid composition or $1 \times 10^3$ cells/ml to $5 \times 10^{10}$ cells/ml of liquid composition,
metabolite(s) at a concentration ranging from about 0.1% to 10%,
media derived nutrient(s) at a concentration ranging from about 0.1% to 10%, and
an agriculturally acceptable excipient at a concentration ranging from about 0.01% to 90%.

In some embodiments, the biostimulant composition as defined above comprises total solids at a concentration ranging from about 0.5% to 50%, crude protein at a concentration ranging from about 0.10% to 70%, and, minerals, carbohydrates and lipids at a concentration ranging from about 0.10% to 30%.

In some embodiments, the biostimulant composition as defined above has a pH ranging between 4 to 10.

In some embodiments, the biostimulant composition of the present disclosure comprising consortium having at least 50% gammaproteobacterial methanotroph, metabolite, media derived nutrient, and optionally an agriculturally acceptable excipient, can be combined with a methanotroph derived hydrolysate composition(s) such as those derived by lysing/processing of methanotrophic cells or other microbial cell based biostimulants known in the art.

In all embodiments of the present disclosure, the biostimulant composition as described above comprising a microbial consortium of whole cells, wherein the consortium comprises at least 50% whole cells of gammaproteobacterial methanotroph provides at least one of the following benefits:
- improves or enhances performance of the plant,
- increases availability or efficient utilization of at least one nutrient selected from but not limited to nitrogen, phosphorus and potassium, by the plant, or
- reduces the need for external addition of at least one nutrient selected from nitrogen, phosphorus and potassium, either individually or as part of a fertilizer.

Application of the Biostimulant Composition

Since multiple benefits are associated with use of the biostimulant composition, the present disclosure therefore also relates to application of the biostimulant composition as described above, to a plant.

In some embodiments, the application of the biostimulant composition to a plant is through a method that comprises contacting or applying the plant biostimulant composition described above to the plant or a part thereof.

In some embodiments, the application of the biostimulant composition or the associated method promotes plant growth and/or performance.

In some embodiments, the application of the biostimulant composition or the associated method improves or enhances performance of the plant.

In some embodiments, the application of the biostimulant composition or the associated method increases availability or efficient utilization of at least one nutrient selected from but not limited to nitrogen, phosphorus and potassium, by the plant.

In some embodiments, the application of the biostimulant composition or the associated method reduces the need for external addition of at least one nutrient selected from nitrogen, phosphorus and potassium, either individually or as part of a fertilizer.

In some embodiments, the method comprises:
- obtaining the plant biostimulant composition comprising gammaproteobacterial methanotroph as described above; and
- contacting the plant or a part thereof, with said plant biostimulant composition, wherein said method promotes plant growth and/or performance.

In some embodiments according to the method of treating plants to promote plant growth, the yield is improved by about 10% to 500% relative to a method not employing the plant biostimulant composition described herein.

In some embodiments according to the method of treating plants to promote plant growth, the yield is improved by about 1% to 250% relative to a method not employing the plant biostimulant composition described herein.

In some embodiments according to the method of treating plants to promote plant growth, the yield is improved by about 1% to 100% relative to a method not employing the plant biostimulant composition described herein.

In some embodiments according to the method of treating plants to promote plant growth, the yield is improved by about 1% to 50% relative to a method not employing the plant biostimulant composition described herein.

In some embodiments according to the method of treating plants to promote plant growth, the yield is improved by about 10% to 10% relative to a method not employing the plant biostimulant composition described herein.

In some embodiments according to the method of treating plants to promote plant growth, the yield is improved by about 1.5 folds to 10 folds relative to a method not employing the plant biostimulant composition described herein.

In some embodiments, the biostimulant composition is contacted or applied in an amount ranging from about 0.1 L/acre to 10 L/acre.

In some embodiments, the biostimulant composition is contacted or applied in an amount ranging from about 0.5 L/acre to 5 L/acre.

In some embodiments, the biostimulant composition is in a solid form or a liquid form, and is contacted with or applied to the plant at a concentration ranging from about 1 ml per litre to about 50 ml per litre of the liquid form or 1 gm per kilogram to about 50 gm per kilogram of the solid form.

In some embodiments, the biostimulant composition is in a solid form or a liquid form, and is contacted with or applied to the plant at a concentration ranging from about 1× to 100000× dilution of the solid or liquid form of the composition, and includes all values and ranges therein.

In some embodiments, the biostimulant composition is in a liquid form or a solid form, selected from but not limited to liquid sprays, dust, granular, beads, soluble powder, wettable powder, pellet, microencapsulated, emulsifiable concentrate, capsular suspension, dry flowable form, liquid Flowable, and the likes. While these forms provide examples of different ways in which the biostimulant composition of the present disclosure can be formulated, the activity of the composition is not dependent on or changes with the change in form. Hence, a person skilled in the art can employ the composition of the present disclosure in a form that suits their purpose the best.

In some embodiments, the biostimulant composition as described above is contacted with or applied to an aerial part of the plant including leaf as a foliar application.

In some embodiments, the biostimulant composition as described above is contacted or applied to the plant through its soil.

In some embodiments, the biostimulant composition is contacted with or applied to a plant through its soil, or through foliar application, as described above, as a single dose, or multiple doses.

In some embodiments, the biostimulant composition as described above is contacted or applied to the plant through its seed.

In some embodiments, the biostimulant composition is contacted with or applied to a plant through its soil, seed or through foliar application, as described above, as a single dose, or multiple doses, wherein each subsequent dose is administered 1 to 90 days apart per crop cycle.

In some embodiments, the application of the biostimulant composition is unaffected or unchanged by the seed rate, planting date, harvest time and other standard/conventional agricultural management practices. Hence, for application of the said composition, a person skilled in the art can freely modulate the said practices depending on the plant or crop in question.

In some embodiments, the amount of the biostimulant composition that is to be applied to a plant is known to a person skilled in the art. The said amount therefore does not form a limiting feature of the present disclosure. The importance lies in the constituents of the composition, most importantly, the microbial consortium, the type of cells therein, and the total number and ratio of cells therein. Depending on the plant, a person skilled in the art will find no difficulty in modulating the dosage of the composition that needs to be applied to a plant, as long as the above criteria are met.

Improving Plant Performance

As mentioned previously, when the biostimulant composition of the present disclosure is applied on or contacted with a plant, it improves or enhances its performance.

Accordingly, the present disclosure provides use of the above-described whole cell biostimulant composition for enhancing or improving agricultural/plant productivity or performance.

In some embodiments, the plant performance is enhanced or improved by applying or contacting the plant or its seed with the whole cell based biostimulant composition as described above.

In some embodiments, the present disclosure provides whole cell-based biostimulant composition comprising gammaproteobacterial methanotrophs, metabolite and media derived nutrient for improving or enhancing plant performance.

In all embodiments of improving or enhancing plant performance, the features of methanotroph (whole cell) based biostimulant composition are as described in one or more of the preceding embodiments.

In some embodiments, enhancement or improvement in agricultural productivity is measured as the differential increase in agricultural productivity (such as crop yield, productivity or other beneficial parameters) when agricultural production is carried out with and without using/applying the biostimulant compositions described herein.

In some embodiments, the plant to which the biostimulant composition of the present disclosure is applied, is selected from but not limited to an agricultural crop, horticultural crop, plantation crop, or any combinations thereof.

In some embodiments, the agricultural crop is selected from a group comprising but not limited to cereals, millets, pulses/legumes, cash crops, oil yielding crops and combinations thereof.

In some embodiments, the horticultural crop is selected from a group comprising but not limited to vegetable crops, medicinal crops, aromatic crops, floricultural crops, fruit crops, spices and plantation crops and combinations thereof.

In some embodiments, the plant is selected from a group comprising but not limited to radish, spinach, coriander, chili, cluster bean, potato, French bean, tomato, lettuce, corn, paddy, marigold, broccoli, soybean, capsicum, grapes, English cucumber, pomegranate, wheat, carrot, maize, Faba bean, sunflower, pea, canola, barley, mint, corn, saffron, and combinations thereof.

In some embodiments, enhancing or improving plant performance includes but is not limited to having a stimulating/promoting effect on plant growth, yield, nutrient use efficiency, or any combinations thereof. In an embodiment, enhancing or improving plant performance comprises having a stimulating/promoting effect on plant as measured by increase in production or number of below ground or aerial biomass such as root, shoot, leaf, flowers, stamens, stigma, anthers, fruits, seeds, increase in photosynthetic activity during control or adverse conditions, improved efficiency with regard to availability, absorption and use of nutrients/minerals, reduced use of chemical fertilizers, improved metabolite accumulation or any combinations thereof.

In some embodiments, improving or enhancing plant performance comprises stimulating or promoting a quantitative or qualitative plant attribute selected from a group comprising biomass production, yield, photosynthetic activity, nutritional value, secondary metabolites and nutrient use efficiency, or any combination thereof.

In some embodiments, effect of the improved or enhanced plant performance is measured through one or more of:
- increase in number, size or quality of below ground or aerial biomass selected from a group comprising root, shoot, leaf, flowers, anthers, stigma, stamens, fruits and seeds or any combination thereof,
- increase in photosynthetic activity or chlorophyll content,
- increase in protein, dietary fibre, β-carotene or essential oil content, plant specific metabolite or any combination thereof,
- efficient absorption or utilization of available or externally provided nutrients or minerals.

In some embodiments a person skilled in the art understands that the attributes and the ways in which they are measured as provided above does not constitute an exhaustive list, and are only provided for exemplification. Enhancement or improvement in any other plant performance attribute or parameter not explicitly captured herein, also falls under the purview of the present disclosure. The importance lies in the fact that a plant is able to grow or survive better when the whole cell biostimulant of the present disclosure is applied to it.

In some embodiments, the biostimulant composition as described above is used for improving the yield and other parameters in cultivation practices selected from a group comprising but not limited to hydroponics, aeroponics, vertical farming, indoor gardening, lawns and combinations thereof.

The present disclosure further relates to a method of improving or enhancing plant performance, said method comprising contacting the plant with the biostimulant composition as described above.

In some embodiments, the method of improving or enhancing plant performance comprises contacting the plant with the biostimulant composition comprising gammaproteobacterial methanotroph, metabolite, media derived nutrient and agriculturally acceptable excipient as described above.

In some embodiments, the method of improving or enhancing plant performance comprises contacting the plant with the biostimulant composition comprising *Methylococcus capsulatus*, metabolite, media derived nutrient and agriculturally acceptable excipient as described above.

In some embodiments according to the method of improving or enhancing plant performance, the plant biostimulant composition as described above is contacted with or applied to an aerial part of the plant including leaf as a foliar application to improve plant performance.

In some embodiments according to the method of improving or enhancing plant performance, the plant biostimulant composition as described above is contacted or applied to soil to improve plant performance.

In some embodiments according to the method of improving or enhancing plant performance, the plant biostimulant composition as described above is contacted or applied to seed of the plant to improve plant performance.

In some embodiments according to the method of improving or enhancing plant performance, the plant biostimulant composition as described above is contacted or applied to an aerial part of the plant including shoot, flower, fruit or any combination thereof to improve plant performance.

In some embodiments according to the method of improving or enhancing plant performance, the plant biostimulant composition as described above is contacted or applied to a seed to improve plant performance. In some embodiments, said plant biostimulant composition is applied as a seed coating, seed dressing or seed treatment.

In some embodiments according to the method of improving or enhancing plant performance, the plant biostimulant composition as described above is contacted with or applied to the whole plant to improve plant performance.

In some embodiments according to the method of improving or enhancing plant performance, the plant biostimulant composition as described above is contacted with or applied to the plant or a part thereof through any known mode of application to improve plant performance.

In some embodiments according to the method of improving or enhancing plant performance, the yield is improved by about 1% to 500% relative to a method not employing the plant biostimulant composition described herein.

In some embodiments according to the method of improving or enhancing plant performance, the yield is improved by about 1% to 250% relative to a method not employing the plant biostimulant composition described herein.

In some embodiments according to the method of improving or enhancing plant performance, the yield is improved by about 1% to 100% relative to a method not employing the plant biostimulant composition described herein.

In some embodiments according to the method of improving or enhancing plant performance, the yield is improved by about 1% to 50% relative to a method not employing the plant biostimulant composition described herein.

In some embodiments according to the method of improving or enhancing plant performance, the yield is improved by about 10% to 10% relative to a method not employing the plant biostimulant composition described herein.

In some embodiments according to the method of improving or enhancing plant performance, the yield is improved by about 1.5 folds to 10 folds relative to a method not employing the plant biostimulant composition described herein.

In some embodiments, application of the biostimulant composition of the present disclosure to a plant results in an increase in biomass production by at least about 23% to about 43%, when compared to a plant where the said composition has not been applied.

In some embodiments, application of the biostimulant composition of the present disclosure to a plant results in an increase in biomass production by at least about 11% to about 15%, when compared to a plant where the said composition has not been applied, and instead a commercially available biostimulant comprising nitrogen fixing, phosphate solubilizing and zinc solubilizing bacteria has been applied.

In some embodiments, application of the biostimulant composition of the present disclosure to a plant results in an increase in its pod yield by at least about 22%, when compared to a plant where the said composition has not been applied.

In some embodiments, application of the biostimulant composition of the present disclosure to a plant results in an increase in its pod yield by at least about 8% to about 15%, when compared to a plant where the said composition has not been applied, and instead a commercially available biostimulant comprising nitrogen fixing, phosphate solubilizing and zinc solubilizing bacteria has been applied.

In some embodiments, application of the biostimulant composition of the present disclosure to a plant results in an increase in plant yield by at least about 27% to about 48%, when compared to a plant where the said composition has not been applied.

In some embodiments, application of the biostimulant composition of the present disclosure to a plant results in an increase in number of tap roots by at least about 7% to about 10%, when compared to a plant where the said composition has not been applied.

In some embodiments, application of the biostimulant composition of the present disclosure to a plant results in an increase in photosynthetic efficiency as measured by SPAD index by at least about 32%, when compared to a plant where the said composition has not been applied.

In some embodiments, application of the biostimulant composition of the present disclosure to a plant results in an increase in dietary fibre content by at least about 20%, when compared to a plant where the said composition has not been applied.

In some embodiments, application of the biostimulant composition of the present disclosure to a plant results in an increase in protein content by at least about 44%, when compared to a plant where the said composition has not been applied.

Nitrogen Fixation

As mentioned previously, one of the ways in which the biostimulant composition of the present disclosure improves or enhances plant performance is by improving the nutrient use efficiency of the plant. One of the most important nutrients that is required for proper growth, development, performance and/or survival of a plant is nitrogen. Hence, if a plant is able to utilize the atmospheric nitrogen efficiently, it will result in better growth, development, performance and/or survival.

Thus, in some embodiments, the plant performance is enhanced or improved as a direct result of increased nitrogen fixation that is facilitated by the biostimulant composition of the present disclosure. Accordingly, when the biostimulant composition of the present disclosure is applied to a plant, it facilitates nitrogen fixation, and makes the nitrogen and associated compounds available to the plant, which in-turn is used by the plant to grow and survive efficiently.

In some embodiments, the biostimulant composition of the present disclosure facilitates increased nitrogen fixation, that results in better plant absorption or utilization of nitrogen/nitrogen derived compounds or metabolites, in-turn resulting in enhanced or improved plant growth, indicated by a quantitative or qualitative plant attribute selected from a group comprising biomass production, yield, photosynthetic activity, nutritional value, secondary metabolites and nutrient use efficiency, or any combination thereof.

The present disclosure therefore provides a method which facilitates better nitrogen fixation in plants resulting in either increased availability of nitrogen to the plant or efficient utilization of nitrogen by the plant, or both.

Thus, the present disclosure provides a method which increased nitrogen fixation in plants resulting in either increased availability of nitrogen to the plant or efficient utilization of nitrogen by the plant, or both.

In some embodiments, better or increased nitrogen fixation is facilitated when the biostimulant composition of the present disclosure is contacted with or applied to the plant. This results in increased availability of nitrogen to the plant or efficient utilization of nitrogen by the plant, or both.

In all embodiments of the method for facilitating better nitrogen fixation, the biostimulant composition employed is as described by any of the embodiments above. The manner in which the biostimulant is contacted with or applied to the plant is also as per any of the embodiments described above. For the sake of brevity, and avoiding repetition, each of those embodiments are not being reiterated here again.

However, each of the said embodiments, completely fall within the purview of the method for facilitating nitrogen fixation in a plant.

In some embodiments, the biostimulant composition increased, enhances, improves or betters the nitrogen fixation in a plant, when compared to nitrogen fixation by the same plant in absence of the biostimulant composition of the present disclosure.

In some embodiments according to the method of improving nitrogen fixation, the method comprises:
developing the biostimulant composition of the present disclosure comprising a microbial culture having at least 50% whole cells of gammaproteobacterial methanotroph, optionally along with other PGPMs, metabolite(s), media derived nutrient(s) and an agriculturally acceptable excipient(s), and
applying the said composition to the plant, wherein the methanotroph in the composition fixes atmospheric nitrogen and improves its availability to the plant.

In some embodiments according to the method of improving nitrogen fixation, the method comprises:
providing methane to grow gammaproteobacterial methanotroph, such as *M. capsulatus*,
developing the biostimulant composition of the present disclosure comprising a microbial culture having at least 50% whole cells of gammaproteobacterial methanotroph, optionally along with other PGPMs, metabolite(s), media derived nutrient(s) and an agriculturally acceptable excipient(s), and
applying the said composition to the plant, wherein the methanotroph in the composition fixes atmospheric nitrogen and improves its availability to the plant, wherein the amount of nitrogen fixed is higher than nitrogen fixed by the same plant without the said composition.

While the availability of nitrogen or efficient utilization of nitrogen is increased through better nitrogen fixation facilitated by the biostimulant composition of the present disclosure, this in-turn is a direct result of increase in expression of genes of nitrogenase cluster selected from a group comprising nifA, nifD, nifH and nifK, or any combination thereof, in the microbial whole cells present in the biostimulant.

Thus, in some embodiments, improvement in nitrogen fixation facilitated by the biostimulant composition of the present disclosure is a result of increase in expression of genes of nitrogenase cluster selected from a group comprising nifA, nifD, nifH and nifK, or any combination thereof, in the gammaproteobacterial methanotroph present in the biostimulant.

In some embodiments, improvement in nitrogen fixation facilitated by the biostimulant composition of the present disclosure is a result of increase in expression of genes of nitrogenase cluster selected from a group comprising nifA, nifD, nifH and nifK, or any combination thereof, in the *M. capsulatus* present in the biostimulant.

In some embodiments, application of the biostimulant composition of the present disclosure to a plant enables the gammaproteobacterial methanotrophs to grow in the absence of external nitrogen source by modulating the expression of Nif genes and thus activating the nitrogenase machinery to fix environmental nitrogen.

In some embodiments, the method reduces need for external addition of nitrogen or nitrogen carrying fertilizer in the plant, by at least about 10% to about 100%, when compared to the need for addition of nitrogen or nitrogen carrying fertilizer in a plant not contacted with the biostimulant composition of the present disclosure.

In a manner similar to above, the biostimulant composition of the present disclosure also facilitates better availability and/or utilization of other nutrients, including phosphorus and potassium to the plant.

Accordingly, the present disclosure also provides a method of increasing availability of phosphorous, potassium or any combination thereof to a plant, the method comprising contacting or applying to the plant, the biostimulant composition as described in any of the embodiments above.

Similarly, the present disclosure also provides a method of increasing availability of all of nitrogen, phosphorous and potassium to a plant, the method comprising contacting or applying to the plant, the biostimulant composition as described in any of the embodiments above. The manner in which the biostimulant is contacted with or applied to the plant is also as per any of the embodiments described above.

In some embodiments, the methods described above increase availability of nitrogen, phosphorous, and potassium, or any combination thereof, in the soil for uptake by the plant.

In some embodiments, the method increases the availability of nitrogen, phosphorous, and potassium or any combination thereof by at least about 10%, 20%, 30%, 40%, 50%, 60%, 70%, 80% or 90% relative to a method not employing the composition defined herein.

In some embodiments, application of the biostimulant composition of the present disclosure to a plant results in an improved uptake of nitrogen by about 36%, when compared to a plant where the said composition has not been applied.

In some embodiments, application of the biostimulant composition of the present disclosure to a plant results in an improved uptake of phosphorus by about 53%, when compared to a plant where the said composition has not been applied.

In some embodiments, application of the biostimulant composition of the present disclosure to a plant results in an improved uptake of potassium by about 39%, when compared to a plant where the said composition has not been applied.

As mentioned previously, one of the important objectives of the present disclosure is to also efficiently utilize the methane generated by agricultural activities and other sources, in a manner that is beneficial in reducing the carbon footprint. Accordingly, use of the biostimulant composition of the present disclosure achieves this objective.

Utilization of Methane & Reduction in its Atmospheric Content

The present disclosure accordingly also provides a method of increasing utilization of atmospheric methane the method comprising: contacting or applying to the plant the biostimulant composition as described above.

Since the biostimulant composition of the present disclosure comprises a microbial consortium that has at least 50% whole cells of gammaproteobacterial methanotroph, it acts as an efficient tool that is employed for utilization of methane. In other words, mere application of this composition to a plant, allows the gammaproteobacterial methanotrophs to utilize the methane that is generated by the same plant, or present in the atmosphere as a result of agricultural activity or generated from any other source, and use it for its growth and survival. As a result, the methane levels in the vicinity of this composition reduce.

In some embodiments, the gammaproteobacterial methanotroph of the present disclosure utilizes methane through carbon capture, and in-turn utilizes it for its growth and survival.

In some embodiments, the utilization of methane by the consortium in the biostimulant composition of the present disclosure comprising at least 50% whole cells of gammaproteobacterial methanotroph, recycles at least about 0.1 kg of methane per kg of biostimulants used.

In some embodiments, the methane utilized by the gammaproteobacterial methanotrophs can be divided into two buckets:
- atmospheric methane that is usually part of the atmospheric dry air, and present at about 1-2 ppm; or
- methane that is concentrated in a particular area as a consequence of high agricultural or industrial activity.

While the gammaproteobacterial methanotrophs present in the consortium of the biostimulant composition herein uses the atmospheric methane as well, the focus of this disclosure is to allow the methanotrophs to utilize the methane concentrated in a particular area, particular due to agricultural activity. In other words, plants that emit high levels of methane, act as important sources of methane for these methanotrophs. Since methane is a harmful greenhouse gas, its concentration in atmosphere needs to be continuously brought down. The use of the biostimulant composition of the present disclosure facilitates exactly that. Since the composition comprises gammaproteobacterial methanotrophs, when applied to a plant, which in-turn produces high levels of methane, the said organisms are able to utilize it, and help in improving nitrogen fixation, and performance of the plant.

In all embodiments related to the method of utilization of methane by the consortium present in the biostimulant composition, the biostimulant composition as such, as well as the manner in which it is to be applied for utilization of the methane by the consortium therein, is as per any of the embodiments of the composition or methods provided above. For the sake of brevity, and avoiding repetition, each of those embodiments are not being reiterated here again. However, each of the said embodiments, completely fall within the purview of the method for facilitating utilization of methane.

As mentioned previously, since the composition provides multiple benefits in terms of enhancing plant performance, and/or increasing nitrogen fixation in plants, utilization of methane by the same composition acts as an added advantage. A combination of these attributes makes the biostimulant composition an extremely efficient, and environmentally friendly product.

Simultaneous Utilization of Methane and Nitrogen Fixation in Plants

The present disclosure accordingly also provides a method for facilitating simultaneous utilization of methane and nitrogen fixation in a plant, said method comprising contacting or applying the biostimulant composition as described above, to the plant.

In some embodiments, the present disclosure provides a method for facilitating simultaneous utilization of methane and nitrogen fixation in a plant, said method comprising contacting or applying the biostimulant composition comprising a microbial consortium of whole cells, wherein the consortium comprises at least 50% whole cells of gammaproteobacterial methanotroph.

In some embodiments, the microbial consortium comprises at least about 60% to about 100% whole cells of gammaproteobacterial methanotroph.

In some embodiments, the gammaproteobacterial methanotroph is a type I or type X methanotroph belonging to genus selected from a group comprising *Methylococcus, Methylomonas, Methylobacter, Methyloglobulus, Methylovulum, Methylomicrobium, Methylosarcina, Methylosphaera, Methyloprofundus, Methylosoma, Methylocucumis, Methylocaldum, Methyloparacoccus, Methylogaea, Methylomagnum, Methyloterricola, Methylothermus, Methylohalobius, Methylomarinovum, Methylomarinum* and *Crenothrix,* or any combination thereof.

In some embodiments, the gammaproteobacterial methanotroph is *Methylococcus capsulatus.*

In some embodiments, the composition is in a solid form or a liquid form, and comprises at least one metabolite, at least one media derived nutrient and optionally at least one agriculturally acceptable excipient.

In some embodiments, the microbial consortium of whole cells comprises about $1 \times 10^3$ cells to about $5 \times 10^{10}$ cells per gram or per millilitre of the composition and constitutes about 0.1% to about 80% of the composition; with the remainder of the composition constituted by about 0.1% to about 10% of at least one metabolite, about 0.1% to about 10% of at least one media derived nutrient and optionally about 0.01% to about 90% of at least one agriculturally acceptable excipient, and includes all values and ranges therein.

In some embodiments, the metabolite is selected from a group comprising carbohydrates, lipids, sugars, fatty acids, proteins, peptides, amino acids, nucleic acid, nucleotides, vitamins, organic acids, salts, minerals, osmolytes, extracellular enzymes, bacterial derived components and minerals, or any combination thereof, wherein the media derived nutrient is selected from a group comprising ions and salts, or a combination thereof, and wherein the agriculturally acceptable excipient is selected from a group comprising carrier, cell protectant, adjuvant, surfactant, stabilizer, preservative, diluent, suspending agent, dispersing agent and cosolvent, or any combination thereof.

In some embodiments, in addition to the gammaproteobacterial methanotroph, the consortium comprises about 10% to about 50% of at least one plant growth-promoting microbe selected from a group comprising nitrogen fixing microorganism, phosphate solubilizing microorganism, mineral solubilizing microorganism, phytohormone secreting microorganism, organic acids secreting bacteria and plant beneficial microbe, or any combination thereof.

Thus, in some embodiments, the microbial consortium of the present disclosure comprises primarily of gammaproteobacterial methanotrophs, such as *M. capsulatus.*

In some embodiments, the microbial consortium of the present disclosure comprises of gammaproteobacterial methanotrophs, such as *M. capsulatus* and one or more PGPMs in a ratio of about 90:10.

In some embodiments, the microbial consortium of the present disclosure comprises of gammaproteobacterial methanotrophs, such as *M. capsulatus* and one or more PGPMs in a ratio of about 80:20.

In some embodiments, the microbial consortium of the present disclosure comprises of gammaproteobacterial methanotrophs, such as *M. capsulatus* and one or more PGPMs in a ratio of about 70:30.

In some embodiments, the microbial consortium of the present disclosure comprises of gammaproteobacterial methanotrophs, such as *M. capsulatus* and one or more PGPMs in a ratio of about 60:40.

In some embodiments, the microbial consortium of the present disclosure comprises of gammaproteobacterial methanotrophs, such as *M. capsulatus* and one or more PGPMs in a ratio of about 50:50.

In some embodiments, the consortium in the composition utilizes methane, facilitates nitrogen fixation and:
improves or enhances performance of the plant,
reduces the need for external addition of at least one nutrient selected from nitrogen, phosphorus and potassium, either individually or as part of a fertilizer, or both.

In all embodiments of the method for facilitating simultaneous utilization of methane and nitrogen fixation in a plant, the biostimulant composition employed is as described by any of the embodiments mentioned above. Similarly, the manner in which the said biostimulant composition is to be applied to a plant, is also as described by any of the embodiments above. For the sake of brevity, and avoiding repetition, each of those embodiments are not being reiterated here again. However, each of the said embodiments, completely fall within the purview of the method for facilitating simultaneous utilization of methane and nitrogen fixation in a plant.

More particularly, the present disclosure provides a method for facilitating simultaneous utilization of methane and nitrogen fixation/availability in a plant, the method comprising contacting or applying to the plant a biostimulant composition comprising a consortium of whole cells comprising at least 50% whole cells of gammaproteobacterial methanotroph, optionally along with metabolite(s), media derived nutrient(s) and agriculturally acceptable excipient(s).

In some embodiment, the gammaproteobacterial methanotroph in the biostimulant composition utilizes atmospheric methane to facilitate/enable nitrogen fixation in plants.

In some embodiments, the methanotrophic organism in the composition of the above method utilizes atmospheric methane to increase nitrogen fixation, and thereby increased nitrogen availability to plants.

In some embodiments, the gammaproteobacterial methanotrophs in the consortium of the composition has an average colonization ability per unit of a plant part of at least about $2 \times 10^8$ bacterial cells per gram of weight of the plant part, specifically roots.

In some embodiments, the plant part is selected from a group comprising root, rhizome, seed, stalk, flower, stigma, stamens, anthers, fruit, leaves, shoot and combinations thereof.

In some embodiments, the gammaproteobacterial methanotrophs in the consortium of the composition defined above is capable of increasing nitrogen availability to the plant by fixing atmospheric nitrogen into soil.

In some embodiments, when the biostimulant composition defined herein is contacted or applied to a plant/crop, the gammaproteobacterial methanotroph in the composition is capable of facilitating the utilization of atmospheric methane along with simultaneous increase in nitrogen availability to the plant by fixing atmospheric nitrogen into soil, relative to a method not employing the composition defined herein.

In some embodiments, the gammaproteobacterial methanotrophs in the composition defined above is capable of utilizing atmospheric methane for its growth and metabolism, and fixing atmospheric nitrogen into soil as ammonia, nitrites, nitrates or other nitrogen containing compounds for enhanced nitrogen uptake and assimilation by plant.

In some embodiments, the plant is a leguminous plant, a non-leguminous plant, or a combination thereof.

In some embodiments, the plant is an agricultural crop, a horticultural crop, a plantation crop, or any combinations thereof.

In some embodiments, the plant is an agricultural crop selected from a group comprising but not limited to cereals, millets, pulses/legumes, cash crops, oil yielding crops and combinations thereof.

In some embodiments, the plant is a horticultural crop selected from a group comprising but not limited to vegetable crops, medicinal crops, aromatic crops, floricultural crops, fruit crops, spices and plantation crops and combinations thereof.

While the availability of nitrogen or efficient utilization of nitrogen is increased through better nitrogen fixation facilitated by the biostimulant composition of the present disclosure, this in-turn is a direct result of increase in expression of genes of nitrogenase cluster selected from a group comprising nifA, nifD, nifH and nifK, or any combination thereof, in the microbial whole cells present in the biostimulant.

Thus, in some embodiments, improvement in nitrogen fixation along with simultaneous utilization of methane, facilitated by the biostimulant composition of the present disclosure is a result of increase in expression of genes of nitrogenase cluster selected from a group comprising nifA, nifD, nifH and nifK, or any combination thereof, in the gammaproteobacterial methanotroph present in the biostimulant.

In some embodiments, improvement in nitrogen fixation along with simultaneous utilization of methane, facilitated by the biostimulant composition of the present disclosure is a result of increase in expression of genes of nitrogenase cluster selected from a group comprising nifA, nifD, nifH and nifK, or any combination thereof, in the *M. capsulatus* present in the biostimulant.

In some embodiments, the consortium in the biostimulant composition of the present disclosure comprising at least 50% whole cells of gammaproteobacterial methanotroph, recycles at least about 0.1 kg of methane per kg of biostimulants used, while facilitating nitrogen fixation as mentioned above.

In some embodiments, the gammaproteobacterial methanotroph of the present disclosure utilizes methane through carbon capture, and in-turn utilizes it for its growth and survival, and facilitating nitrogen fixation.

As mentioned previously, since the biostimulant composition of the present disclosure facilitates better availability of at least one nutrient selected from but not limited to nitrogen, phosphorus and potassium to the plant, or increases utilization of the said nutrients by the plant, the need for external addition of artificial/chemical/synthetic fertilizers comprising these nutrients is therefore automatically reduced.

Reduction in Need of External Nutrients and Fertilizers

Accordingly, the present disclosure provides a method of reducing need of external addition of at least one nutrient or nutrient carrying fertilizer for growth, development, performance and/or survival of a plant, said method comprising contacting or applying the biostimulant composition as described above, to the plant.

In some embodiments, the nutrient is selected from a group comprising but not limited to nitrogen, phosphorus and potassium, or any combination thereof.

In some embodiments, the fertilizer is a chemical fertilizer.

In some embodiments, the method comprises reducing the input of chemical fertilizer required for growth and productivity of a plant, the method comprising contacting or applying to the plant the biostimulant composition of the present disclosure.

In some embodiments, contacting or applying the biostimulant composition to the plant decreases the usual conventional amount of nitrogen containing fertilizer, phosphorous containing fertilizer, potassium containing fertilizer, or any combination thereof, required for producing an improved yield of the plant.

In some embodiments, a person skilled in the art readily knows and understands the amount of said fertilizers conventionally employed during the normal course of agriculture. The biostimulant composition of the present disclosure reduces the need for such external additional of said fertilizers.

In some embodiments, contacting or applying the biostimulant composition to the plant decreases the amount of nitrogen containing fertilizer comprising glutamine, ammonia, ammonium, urea, sulphur coated urea, methylene urea, polymer coated urea, isobutylidene diurea, nitrate, nitrite, ammonium containing molecules, nitrate containing molecules or nitrite containing molecules, or any combinations thereof, required for producing an improved yield of the plant.

In some embodiments, contacting or applying the biostimulant composition to the plant decreases the amount of phosphorous containing fertilizer comprising but not limited to diammonium phosphate, monoammonium phosphate, single super phosphate, ammonium dihydrogen phosphate, ammonium phosphate, super phosphate, tricalcium phosphate or any combinations thereof as a source of phosphate.

In some embodiments, contacting or applying the composition to the plant decreases the amount of potassium containing fertilizer comprising but not limited to muriate of potash, sulphate of potash, potassium nitrate, sulfate potash magnesia, kainite or a combination thereof as a source of potassium.

In some embodiments, the method reduces need for external addition of at least one of nitrogen, phosphorus and potassium for growth, development, performance and/or survival of the plant, by at least about 10% to about 100%, when compared to the need for addition of respective nitrogen, phosphorus and potassium in a plant not contacted with the biostimulant composition of the present disclosure.

In some embodiments, the method decreases the amount of chemical fertilizer required for growth of a plant by at least about 10% relative to a method not employing the biostimulant composition defined herein.

In some embodiments, the method decreases the amount of chemical fertilizer required for growth of a plant by at least about 10%, 20%, 30%, 40%, 50%, 60%, 70%, 80% or 90% relative to a method not employing the biostimulant composition defined herein.

In some embodiments, application of the biostimulant composition of the present disclosure with 50% less amount of traditional NPK fertilizer to a plant results in an increase in biomass production by at least about 50%, when compared to a plant grown under the same conditions of 50% less NPK fertilizer and where the said composition has not been applied.

In some embodiments, application of the biostimulant composition of the present disclosure with 50% less amount of traditional NPK to a plant results in an increase in biomass production by at least about 42%, when compared to a plant grown in the regular 100% NPK and where the said composition has not been applied.

In some embodiments, the present disclosure provides a method of reducing need of external addition of at least one nutrient or nutrient carrying fertilizer for growth, development, performance and/or survival of a plant, said method comprising contacting or applying the biostimulant composition comprising a microbial consortium of whole cells, wherein the consortium comprises at least 50% whole cells of gammaproteobacterial methanotroph.

In some embodiments, the microbial consortium comprises at least about 60% to about 100% whole cells of gammaproteobacterial methanotroph, and includes all values and ranges therein.

In some embodiments, the gammaproteobacterial methanotroph is a type I or type X methanotroph belonging to genus selected from a group comprising *Methylococcus, Methylomonas, Methylobacter, Methyloglobulus, Methylovulum, Methylomicrobium, Methylosarcina, Methylosphaera, Methyloprofundus, Methylosoma, Methylocucumis, Methylocaldum, Methyloparacoccus, Methylogaea, Methylomagnum, Methyloterricola, Methylothermus, Methylohalobius, Methylomarinovum, Methylomarinum* and *Crenothrix*, or any combination thereof.

In some embodiments, the gammaproteobacterial methanotroph is *Methylococcus capsulatus*.

In some embodiments, the composition is in a solid form or a liquid form, and comprises at least one metabolite, at least one media derived nutrient and optionally at least one agriculturally acceptable excipient.

In some embodiments, the microbial consortium of whole cells comprises about $1\times10^3$ cells to about $5\times10^{10}$ cells per gram or per millilitre of the composition and constitutes about 0.10% to about 80% of the composition; with the remainder of the composition constituted by about 0.1% to about 10% of at least one metabolite, about 0.1% to about 10% of at least one media derived nutrient and optionally about 0.01% to about 90% of at least one agriculturally acceptable excipient, and includes all values and ranges therein.

In some embodiments, the metabolite is selected from a group comprising carbohydrates, lipids, sugars, fatty acids, proteins, peptides, amino acids, nucleic acid, nucleotides, vitamins, organic acids, salts, minerals, osmolytes, extracellular enzymes, bacterial derived components and minerals, or any combination thereof, wherein the media derived nutrient is selected from a group comprising ions and salts, or a combination thereof, and wherein the agriculturally acceptable excipient is selected from a group comprising carrier, cell protectant, adjuvant, surfactant, stabilizer, preservative, diluent, suspending agent, dispersing agent and cosolvent, or any combination thereof.

In some embodiments, in addition to the gammaproteobacterial methanotroph, the consortium comprises about 10% to about 50% of at least one plant growth-promoting microbe selected from a group comprising nitrogen fixing microorganism, phosphate solubilizing microorganism, mineral solubilizing microorganism, phytohormone secreting microorganism, organic acids secreting bacteria and plant beneficial microbe, or any combination thereof.

In some embodiments, the consortium in the composition reduces the need for external addition of at least one nutrient selected from nitrogen, phosphorus and potassium, either individually or as part of a fertilizer, and:
improves or enhances performance of the plant,
simultaneously utilizes methane and facilitates nitrogen fixation, or
both.

In all embodiments of the method for of reducing need of external addition of at least one nutrient or nutrient carrying fertilizer for growth, development, performance and/or survival of a plant, the biostimulant composition employed is as described by any of the embodiments mentioned above. Similarly, the manner in which the said biostimulant composition is to be applied to a plant, is also as described by any of the embodiments above.

For the sake of brevity, and avoiding repetition, each of those embodiments are not being reiterated here again. However, each of the said embodiments, completely fall within the purview of the method of reducing need of external addition of at least one nutrient or nutrient carrying fertilizer.

In some embodiments of the above method of decreasing an amount of fertilizer required for growth of a plant, the plant is a leguminous plant, a non-leguminous plant, or a combination thereof.

In some embodiments of the above method of decreasing an amount of fertilizer required for growth of a plant, the plant is an agricultural crop, a horticultural crop, plantation crop, or any combinations thereof.

In some embodiments of the above method of decreasing an amount of fertilizer required for growth of a plant, the plant is an agricultural crop selected from a group comprising cereals, millets, pulses/legumes, cash crops, oil yielding crops and combinations thereof.

In some embodiments of the above method of decreasing an amount of fertilizer required for growth of a plant, the plant is a horticultural crop selected from a group comprising vegetable crops, medicinal crops, aromatic crops, floricultural crops, fruit crops, spices and plantation crops, and combinations thereof.

The present disclosure further relates to a method of maintaining soil fertility comprising planting a plant or a part thereof contacted or applied with the biostimulant composition of the present disclosure.

In some embodiments according to the method of maintaining soil fertility, the method further comprises harvesting the said plant.

In some embodiments according to the method of maintaining soil fertility, the method comprises sowing seed contacted or applied with the biostimulant composition of the present disclosure.

In some embodiments according to the method of maintaining soil fertility, the method maintains nitrogen levels of the soil and reduces the need of fertilizer required for plant growth, preferably nitrogen containing fertilizer.

In some embodiments according to the method of maintaining soil fertility, the method reduces the need of nitrogen containing fertilizer, phosphorous containing fertilizer, potassium containing fertilizer, or any combination thereof.

While the preceding embodiments highlighted the importance of the biostimulant composition of the present disclosure, and how it impacts the performance of a plant, the following embodiments provide a process for preparing the said composition comprising a microbial consortium having at least 50% whole cells of gammaproteobacterial methanotroph, optionally along with at least one metabolite, at least one media derived nutrient, and at least one agriculturally acceptable excipient.

Preparing the Biostimulant Composition

The present disclosure accordingly also relates to a process for preparing the biostimulant composition comprising gammaproteobacterial methanotroph, with at least one of a metabolite, or media derived nutrient and optionally at least one agriculturally acceptable excipient as defined above, the process comprising:

obtaining a mixture comprising gammaproteobacterial methanotroph, at least one of metabolite and media derived nutrient; and optionally adding the agriculturally acceptable excipient to the mixture to prepare the composition, or mixing the gammaproteobacterial methanotroph, at least one of metabolite and media derived nutrient, optionally along with the agriculturally acceptable excipient to prepare the composition.

In some embodiments, the process comprises:

obtaining a mixture comprising gammaproteobacterial methanotroph, at least one metabolite and at least one media derived nutrient; and optionally adding the agriculturally acceptable excipient to the mixture to prepare the composition, or mixing the gammaproteobacterial methanotroph, at least one metabolite and at least one media derived nutrient, optionally along with the agriculturally acceptable excipient to prepare the composition.

In some embodiments of the above method, gammaproteobacterial methanotroph is present in a consortium having a total concentration of whole cells ranging from about $1 \times 10^3$ cells to about $5 \times 10^{10}$ cells/g or ml of solid composition, and includes all values and ranges therein.

The present disclosure accordingly also relates to a process for preparing the biostimulant composition comprising gammaproteobacterial methanotroph, optionally along with at least one metabolite, at least one media derived nutrient and at least one agriculturally acceptable excipient as defined above, the process comprising:

fermentation in presence of a methane source to obtain gammaproteobacterial methanotrophs, processing of the fermentation broth containing the cells, and combining the cells, with at least one metabolite, media derived nutrient and/or agriculturally acceptable excipient, to prepare the biostimulant composition of the present disclosure.

In some embodiments, the process comprises:

culturing gammaproteobacterial methanotrophs in a nutrient mixture (culture media) in presence of methane as the sole carbon and energy source, and harvesting the gammaproteobacterial methanotrophs together with metabolite(s) and media derived nutrient(s) to obtain the biostimulant composition of the present disclosure.

In some embodiments, the process comprises:

culturing gammaproteobacterial methanotrophs in a nutrient mixture (culture media) in presence of methane as the sole carbon and energy source, harvesting the gammaproteobacterial methanotrophs together with metabolite(s) and media derived nutrient(s) to obtain a mixture, and optionally adding agriculturally acceptable excipient(s) to the mixture, to obtain the biostimulant composition of the present disclosure.

In some embodiments, the gammaproteobacterial methanotroph is *Methylococcus capsulatus*.

Thus, in some embodiments, the process comprises culturing *Methylococcus capsulatus* in culture media under suitable culturing conditions, followed by harvesting the said *Methylococcus capsulatus*, to prepare the biostimulant composition of the present disclosure.

In some embodiments, the process comprises:
fermenting or culturing the *Methylococcus capsulatus* in a culture media in presence of methane under suitable conditions of temperature and pressure,
harvesting the *Methylococcus capsulatus* together with metabolite(s) and media derived nutrient(s) to obtain the biostimulant composition of the present disclosure.
culturing *Methylococcus capsulatus* in a nutrient mixture (culture media) in presence of methane under suitable conditions of temperature and pressure,
harvesting the *Methylococcus capsulatus* together with metabolite(s) and media derived nutrient(s) to obtain a mixture comprising *Methylococcus capsulatus*, metabolite and non-cellular nutrient, and
optionally In some embodiments, the process comprises:
culturing *Methylococcus capsulatus* to obtain a mixture comprising *Methylococcus capsulatus* cells, metabolite(s) and media derived nutrient(s); and
optionally adding the agriculturally acceptable excipient to the mixture to prepare the biostimulant composition of the present disclosure.

In some embodiments, the process comprises:
adding agriculturally acceptable excipient(s) to the mixture, to obtain the biostimulant composition of the present disclosure.

In exemplary embodiments of the present disclosure, the method of culturing methanotrophs is carried out according to the description and examples in applications PCT/IB2017/052688 and/or PCT/IB2019/059664, the description of which in entirety is incorporated herein.

In exemplary embodiments of the present disclosure, the method of culturing *Methylococcus capsulatus* is carried out according to PCT/IB2017/052688 and/or PCT/IB2019/059664, the description of which in entirety is incorporated herein. In other exemplary embodiments of the present disclosure, the method of culturing *Methylococcus capsulatus* in a culture media in presence of methane under suitable culturing conditions is described in PCT/IB2017/052688 and/or PCT/IB2019/059664, the description of which in entirety is incorporated herein.

In some embodiments, post culturing, the cells together with media derived components are mixed with at least one agriculturally acceptable excipient.

In some embodiments, the excipient used is selected from known adjuvants and cell protectants, and employed at 0.01%, 0.5% or 1% (w/v) in the composition.

In some embodiments, post fermentation process, the methanotrophic cells together with media derived components are mixed with at least one group of bacteria wherein the bacteria is from a group comprising nitrogen fixing, mineral solubilizing, phytohormone producing bacteria or plant growth promoting bacteria.

In some embodiments of the method described above, the prepared composition comprises *Methylococcus capsulatus*, at least one metabolite selected from but not limited to carbohydrates, sugars, proteins, amino acids, nucleic acids, nucleotides, peptides, fatty acids, lipids, vitamins, organic acids, osmolytes and salts, and at least one media derived nutrient selected from but not limited to salts, minerals and ions.

As mentioned previously, the biostimulant composition of the present disclosure comprises a consortium of microorganisms, that comprises a total of about $1 \times 10^3$ whole cells 10 to about $5 \times 10^{10}$ whole cells per gram or per millilitre of the compositions of the present disclosure. In some embodiments, the microbial consortium comprises a total of about $5 \times 10^3$ whole cells to about $5 \times 10^{10}$ whole cells. In other embodiments, the microbial consortium comprises a total of about $1 \times 10^3$ whole cells to about $1 \times 10^{10}$ whole cells.

Importantly, this consortium must comprise at least 50% whole cells of gammaproteobacterial methanotroph. In some embodiments, the microbial consortium within the biostimulant composition comprises at least about 60% to about 100% whole cells of gammaproteobacterial methanotroph, and includes all values and ranges therein.

Thus, while following the process steps for preparing the biostimulant composition of the present disclosure, inclusion of the gammaproteobacterial methanotroph such as *M. capsulatus* is of primary importance. When the consortium within the composition comprises only gammaproteobacterial methanotroph such as *M. capsulatus*, the process steps are as provided above, whereby the culturing, harvesting, and combining of the cells with metabolite(s), media derived nutrient(s) and/or excipient(s) is applicable with the respective gammaproteobacterial methanotroph cells. However, in cases wherein apart from the gammaproteobacterial methanotroph, other PGPMs are present as part of the consortium, such PGPMs are either also cultured and/or harvested along with the gammaproteobacterial methanotroph, or are cultured and/or harvested separately and then included in the composition as an additional step, to the processes described in the preceding embodiments.

A person skilled in the art will understand that the sequence of steps and the process for culturing and harvesting of cells, and their combination with metabolite(s), media derived nutrient(s) and/or excipient(s) is routine in the art, and can hence be carried out by any know technique. The importance lies in the fact that the final biostimulant composition so prepared must fulfil the following:

comprises a microbial consortium of whole cells, wherein the consortium comprises at least 50% whole cells of gammaproteobacterial methanotroph;

comprises total whole cell at a concentration ranging from about $1 \times 10^3$ cells to about $5 \times 10^{10}$ cells per gram or per millilitre of the composition; and optionally comprises at least one metabolite at a concentration ranging from about 0.1% to about 10%;

optionally comprises at least one media derived nutrient at a concentration ranging from about 0.1% to about 10%; and optionally comprises at least one agriculturally acceptable excipient at a concentration ranging from about 0.01% to about 90%.

In some embodiments, the gammaproteobacterial methanotroph employed in the biostimulant composition is a type I or type X methanotroph belonging to genus selected from a group comprising *Methylococcus, Methylomonas, Methylobacter, Methyloglobulus, Methylovulum, Methylomicrobium, Methylosarcina, Methylosphaera, Methyloprofundus, Methylosoma, Methylocucumis, Methylocaldum, Methyloparacoccus, Methylogaea, Methylomagnum, Methyloterricola, Methylothermus, Methylohalobius, Methylomarinovum, Methylomarinum* and *Crenothrix*, or any combination thereof.

In some embodiments, the gammaproteobacterial methanotroph employed in the biostimulant composition is a type I or type X methanotroph is selected from a group comprising *Methylococcus* sp., *Methylomonas* sp., *Methylobacter* sp., *Methyloglobulus* sp., *Methylovulum* sp., *Methylomicrobium* sp., *Methylosarcina* sp., *Methylosphaera* sp., *Methyloprofundus* sp., *Methylosoma* sp., *Methylocucumis* sp., *Methylocaldum* sp., *Methyloparacoccus* sp., *Methylogaea* sp., *Methylomagnum* sp., *Methyloterricola* sp., *Methylothermus* sp., *Methylohalobius* sp., *Methylomarinovum* sp. *Methylomarinum* sp., and *Crenothrix* sp., or any combination thereof.

In some embodiments, the gammaproteobacterial methanotroph is selected from a group comprising *Methylococcus capsulatus, Methylococcus mobilis, Methylomicrobium kenyense, Methylomicrobium alcaliphilum, Methylomicrobium alcaliphilum* 20Z, *Methylomicrobium* buryatense 5G, *Methylomicrobium* buryatense 4G, *Halomonas pantelleriensis, Methylomicrobium album, Methylomonas methanica,* MB 126, *Methylobacter tundripaludum, Methylovulum miyakonense, Methylomonas rubra, Methylomonas koyamae, Methylomonas methancia, Methylomonas denitrificans, Methylomonas paludis, Methylomonas lenta, Methylomarinum vadi, Methylococcus thermophilus, Methylobacter whittenburyi, Crenothrix polyspora, Clonothrix fusca, Methylobacter bovis, Methylomonas aurantiaca, Methylomonas fodinarum, Methylobacter vinelandii, Methylomicrobium japanense, Methylococcaceae bacterium, Methylocystis methanolicus, Methylocucumis oryzae, Methylogaea oryzae, Methylosarcina lacus, Methylosoma difficile* and combinations thereof.

In an embodiment of the above process of preparing the composition, the methanotroph, the metabolite, the media derived nutrient and the agriculturally acceptable excipient are as described in the preceding embodiments.

In some embodiments, the present disclosure also provides a process for preparing a composition comprising:
- a microbial consortium comprising one or more gammaproteobacterial methanotroph and one or more plant growth-promoting microbe (PGPM),
- at least one metabolite,
- at least one media derived nutrient, and
- optionally, an agriculturally acceptable excipient,
- said process comprising:
  - obtaining a mixture comprising microbial consortium having gammaproteobacterial methanotroph and at least one PGPM, at least one metabolite and at least one media derived nutrient; and optionally adding the agriculturally acceptable excipient to the mixture, to prepare the composition, or
  - obtaining a mixture comprising gammaproteobacterial methanotroph, at least one metabolite and at least one media derived nutrient; and adding at least one plant growth-promoting microbe (PGPM) along with optional addition of the agriculturally acceptable excipient to the mixture, to prepare the composition, or
  - mixing the microbial consortium, at least one metabolite, at least one media derived nutrient, optionally along with the agriculturally acceptable excipient to prepare the composition.

In some embodiments of the process described above, obtaining the mixture comprising microbial consortium, metabolite and media derived nutrient comprises act of culturing the methanotroph and the plant growth-promoting microbe (PGPM) in the same or different culture medium under suitable culturing conditions to obtain a mixture.

In some embodiments, to prepare the composition of the present disclosure, *Methylococcus capsulatus* was cultured in culture media in presence of methane under suitable culturing conditions. Since culturing of *Methylococcus capsulatus* and its growth requirements are well known in the art, conventional process to this effect was employed. These culture conditions were carried out according to the description and examples in applications PCT/IB2017/052688 and/ or PCT/IB2019/059664, the description of which in entirety is incorporated in this example. Post culturing, the cells together with media derived components were mixed with at least one agriculturally acceptable excipient and used for plant performance analysis. In another instance, post fermentation process, methanotrophic cells together with media derived components were mixed with at least one group of bacteria wherein the bacteria were from a group comprising nitrogen fixing, mineral solubilizing, phytohormone producing bacteria or plant growth promoting bacteria. Different ratios of methanotrophic cells were mixed with said bacteria. The ratio of cells to bacteria was accordingly varied from 90:10, 80:20, 70:30, 60:40 or 50:50.

Thus, in some embodiments, the microbial consortium of the present disclosure comprises primarily of *M. capsulatus*. In some embodiments, the microbial consortium of the present disclosure comprises of *M. capsulatus* and one or more PGPMs in a ratio of about 90:10.

In some embodiments, the microbial consortium of the present disclosure comprises of *M. capsulatus* and one or more PGPMs in a ratio of about 80:20.

In some embodiments, the microbial consortium of the present disclosure comprises of *M. capsulatus* and one or more PGPMs in a ratio of about 70:30.

In some embodiments, the microbial consortium of the present disclosure comprises of *M. capsulatus* and one or more PGPMs in a ratio of about 60:40.

In some embodiments, the microbial consortium of the present disclosure comprises of *M. capsulatus* and one or more PGPMs in a ratio of about 50:50.

In some embodiments, typically, the concentration of methanotrophic cells such as *M. capsulatus* in the composition was targeted to be greater than 90%. In some embodiments, the concentration of methanotrophic cells such as *M. capsulatus* in the composition was targeted to be greater than 80%. In some embodiments, the concentration of methanotrophic cells such as *M. capsulatus* in the composition was targeted to be greater than 70%. In some embodiments, the concentration of methanotrophic cells such as *M. capsulatus* in the composition was targeted to be greater than 60%.

In some embodiments, at least 50% of methanotrophic cells such as *M. capsulatus* were mixed with at least 50% of cells from one group of nitrogen fixing, mineral solubilizing, phytohormone producing bacteria or plant growth promoting bacteria.

In some embodiments, the above composition is mixed with at least one agriculturally acceptable excipient. In some embodiments, the excipient used is selected from known adjuvants and cell protectants. In some embodiments, the excipient is combined at 0.010%, 0.1%, 0.5% or 1% (w/v) in the composition.

In some embodiments, the composition contained *M. capsulatus* cells at $1 \times 10^5$ to $1 \times 10^8$ cells/ml harvested post fermentation done in the presence of methane. The composition contains 2-3% of protein and 1-2% of total salts (micronutrients). This composition is formulated with agriculturally acceptable excipient at 0.5%. In some embodiments, the excipient used is 0.5% DMSO. In other embodiments, the excipient used is 0.5% DMSO and 2% Xantham gum. This composition is therefore forms the biostimulant composition of the present disclosure where the microbial consortium comprises primarily of *M. capsulatus*.

In some embodiments, the total protein is analyzed using HPLC and Kjeldahl using established methods, and the micronutrients are analyzed using Inductively coupled plasma-optical emission spectrometry (ICP-OES) and Ion Chromatography (IC).

In some embodiments, cells from the *M. capsulatus* fermentation broth are mixed with phosphate solubilizing bacteria at a ratio of 90:10 with the total cells in the composition being $1\times10^5$ to $1\times10^8$ cells/ml. The composition contains 2-3% of protein and 1-2% of total salts (micronutrients). This composition is formulated with agriculturally acceptable excipient at 0.5%. In some embodiments, the excipient used is 0.5% DMSO. In other embodiments, the excipient used is 0.5% DMSO and 2% Xantham gum. Accordingly, in some embodiments, the ratio of cells from *M. capsulatus* fermentation to PGPMs, such as phosphate solubilizing bacteria, is 90:10, 80:20, 70:30, 60:40 or 50:50. These compositions therefore form the biostimulant compositions of the present disclosure where the microbial consortium comprised of *M. capsulatus* along with other plant growth promoting microorganisms.

In some embodiments, for using the composition on plant, the compositions are in liquid form, and based on the end use, sufficient amount (q.s.) of water was added to each of the compositions prepared herein.

In some embodiments, the composition is used on plants as a solid formulation. For preparation of solid formulation, the composition is mixed with carrier materials and dried to <10% total moisture in the formulation. The composition is dried by air drying, spray drying, drum drying or vacuum tray drying.

In some embodiments of the process described above, the microbial consortium, the methanotroph, the plant growth-promoting microbe (PGPM), the metabolite, media derived nutrient, the agriculturally acceptable excipient, and the concentrations/amounts of said components in the composition are defined in the preceding embodiments.

As mentioned previously, the so prepared biostimulant composition of the present disclosure is important from agricultural and environmental perspective as it fulfills multiple attributes, and overcomes the challenges with respect to high content of methane released by agricultural activities, better agricultural productivity and reduced usage of external fertilizers, all at once—something not provided by any currently available biostimulant.

Uses of the Biostimulant Composition

Thus, the present disclosure also provides for use of the biostimulant composition of the present disclosure, for:
improving or enhancing plant performance, or
facilitating simultaneous utilization of methane and nitrogen fixation in a plant, or
reducing need of external addition of at least one nutrient or nutrient carrying fertilizer for growth, development, performance and/or survival of a plant, or
increasing nitrogen fixation in a plant, or
any combination thereof.

In some embodiments, improving or enhancing plant performance is characterized by at least one of the following:
stimulation or promotion of a quantitative or qualitative plant attribute selected from a group comprising biomass production, yield, photosynthetic activity, nutritional value, secondary metabolites and nutrient use efficiency, or any combination thereof,
increase in number, size or quality of below ground or aerial biomass selected from a group comprising root, shoot, leaf, flowers, anthers, stigma, stamens, fruits and seeds, or any combination thereof,
increase in photosynthetic activity or chlorophyll content, increase in protein, dietary fibre, β-carotene or essential oil content, plant specific metabolites, or any combination thereof, or
efficient absorption or use of available or externally provided nutrient selected from a group comprising nitrogen, phosphorus and potassium, or any combination thereof.

In some embodiments, the biostimulant composition is in a solid form or a liquid form, and is contacted or applied to the plant through its soil, or through aerial or non-aerial parts of the plant selected from a group comprising root, shoot, leaf, flower, anther, stigma, stamen, fruit and seed, or any combination thereof, at a concentration ranging from about 1 ml per litre to about 50 ml per litre of the liquid form or 1 gm per kilogram to about 50 gm per kilogram of the solid form.

In some embodiments, the biostimulant composition is in a solid form or a liquid form, and is contacted or applied to the plant through its soil, or through aerial or non-aerial parts of the plant selected from a group comprising root, shoot, leaf, flower, anther, stigma, stamen, fruit and seed, or any combination thereof, at a concentration ranging from $1\times$ to $100000\times$ dilution of the solid or liquid form of the composition, and includes all values and ranges therein.

The present disclosure also provides use of the biostimulant composition of the present disclosure in a method of making an agricultural or horticultural product, comprising:
a) contacting or applying the biostimulant composition of the present disclosure to a crop; and
b) harvesting the crop to obtain an agricultural or horticultural product.

In some embodiments, the agricultural or horticultural product is selected from the group comprising but not limited to food grain, vegetable, fruit, tuber, nut, cereals, grains, millets, pulses, oil yielding crops, floricultural crops, medicinal plants, aromatic plants, spices and plantation crops, grasses and combinations thereof.

The present disclosure also provides a biostimulant product comprising:
a) the biostimulant composition of the present disclosure; and
b) a hydrolysate based biostimulant composition comprising a protein-derived component in an amount of about 30% or less with respect to weight of the composition; wherein said protein-derived component is obtained from a methanotrophic bacterium.

In all embodiments of the method of use provided herein, the biostimulant composition employed is as described by any of the embodiments mentioned above. Similarly, the manner in which the said biostimulant composition is to be applied to a plant, is also as described by any of the embodiments above. For the sake of brevity, and avoiding repetition, each of those embodiments are not being reiterated here again. However, each of the said embodiments, completely fall within the purview of the said use.

Thus, the present disclosure generally aims at providing unique and alternate approaches/methods for achieving reduction of agricultural methane emissions (by efficient utilization of said methane) and nitrogen availability/fixation in plants simultaneously. To achieve the same, the gammaproteobacterial methanotroph based biostimulant compositions as described above are provided. Additionally, while said methods employing the compositions relate to an environmental friendly approach to reduce methane in atmosphere, fix atmospheric nitrogen to plants and/or reduce the usage of chemical fertilizers along with other advantages, said compositions are also used for agricultural applications to improve the performance of plants/crops.

It is important to understand that fermentation is an economical and scalable process that has been leveraged for decades to bring to market products for various sectors including food, feed, health, consumer products and others. The compositions and methods of the present disclosure have leveraged use of harmful greenhouse gas methane for enabling unique biostimulant compositions. This allows the said biostimulant compositions to be economical/cost effective while enabling sustainability and consistency in its production. The improvement in plant performance results in attractive returns to the users, who are primarily the agri-community and farmer enabling wider adoption of the said biostimulant composition.

Additional embodiments and features of the present disclosure will be apparent to one of ordinary skill in art based upon description provided herein. The embodiments herein provide various features and advantageous details thereof in the description. Descriptions of well-known/conventional methods and techniques are omitted so as to not unnecessarily obscure the embodiments herein. Further, the disclosure herein provides for examples illustrating the above described embodiments, and in order to illustrate the embodiments of the present disclosure certain aspects have been employed. The examples used herein for such illustration are intended merely to facilitate an understanding of ways in which the embodiments herein may be practiced and to further enable those of skill in the art to practice the embodiments herein. Accordingly, the following examples should not be construed as limiting the scope of the embodiments herein.

EXAMPLES

Materials Employed

The *Methylococcus capsulatus* strain employed in the present disclosure has been deposited in accordance with the Budapest Treaty with the Microbial Type Culture Collection (MTCC) and Gene Bank (MTCC 25398). The geographical origin and source of the strain is UK, and upon procurement, the strain was maintained at String Bio Private Limited. Further, all plants/crops which were employed in the below experiments/examples only to validate the technical effects of the product of present disclosure (methanotroph derived biostimulant composition). None of these plants/crops were employed in preparing/developing said biostimulant product of the present disclosure.

Example A

Preparation of Methanotroph Based Whole Cell Composition

To prepare the composition of the present disclosure, *Methylococcus capsulatus* was cultured in culture media in presence of methane under suitable culturing conditions. Since culturing of *Methylococcus capsulatus* and its growth requirements are well known in the art, conventional process to this effect was employed. These culture conditions were carried out according to the description and examples in applications PCT/IB2017/052688 and/or PCT/IB2019/059664, the description of which in entirety is incorporated in this example.

Post culturing, the cells together with media derived components were mixed with at least one agriculturally acceptable excipient and used for plant performance analysis. In another instance, post fermentation process, methanotrophic cells together with media derived components were mixed with at least one group of bacteria wherein the bacteria were from a group comprising nitrogen fixing, mineral solubilizing, phytohormone producing bacteria or plant growth promoting bacteria. Different ratios of methanotrophic cells were mixed with said bacteria. The ratio of cells to bacteria was accordingly varied from 90:10, 80:20, 70:30, 60:40 or 50:50.

Typically, the concentration of methanotrophic cells in the composition was targeted to be greater than 90%. In some instances, the concentration of methanotrophic cells in the composition was targeted to be greater than 80%. In some instances, the concentration of methanotrophic cells in the composition was targeted to be greater than 70%. In some instances, the concentration of methanotrophic cells in the composition was targeted to be greater than 60%. In other instances, 50% of methanotrophic cells were mixed with 50% of cells from one group of nitrogen fixing, mineral solubilizing, phytohormone producing bacteria or plant growth promoting bacteria. This composition was then mixed with at least one agriculturally acceptable excipient. The excipient used was selected from known adjuvants and cell protectants. The excipient was combined at 0.01%, 0.1%, 0.5% or 1% (w/v) in the composition.

In one instance of preparing the composition, the composition contained *M. capsulatus* cells at $1 \times 10^5$ to $1 \times 10^8$ cells/ml harvested post fermentation done in the presence of methane. The composition when analyzed for protein contained 2-3% of protein and 1-2% of total salts (micronutrients). The total protein was analyzed using HPLC and Kjeldahl using established methods. The micronutrients were analyzed using Inductively coupled plasma-optical emission spectrometry (ICP-OES) and Ion Chromatography (IC). This composition was formulated with agriculturally acceptable excipient at 0.5%. In some instances, the excipient used was 0.5% DMSO. In other instances, the excipient was 0.5% DMSO and 2% Xantham gum. This composition is therefore an example of the biostimulant composition of the present disclosure where the microbial consortium comprised primarily of *M. capsulatus*.

In another instance of preparing the composition, cells from the *M. capsulatus* fermentation were mixed with phosphate solubilizing bacteria at a ratio of 90:10 with the total cells in the composition being $1 \times 10^5$ to $1 \times 10^8$ cells/ml. The composition when analyzed for protein contained 2-3% of protein and 1-2% of total salts (micronutrients). This composition was formulated with agriculturally acceptable excipient at 0.5%. In some instances, the excipient used was 0.5% DMSO. In other instances, the excipient was 0.5% DMSO and 2% Xantham gum. The ratio of cells from *M. capsulatus* fermentation to phosphate solubilizing bacteria was accordingly varied from 90:10, 80:20, 70:30, 60:40 or 50:50. These compositions therefore are examples of the biostimulant compositions of the present disclosure where the microbial consortium comprised of *M. capsulatus* along with other plant growth promoting microorganisms.

For using the composition on plant, in some instances the compositions are in liquid form, and based on the end use, sufficient amount (q.s.) of water was added to each of the compositions prepared herein.

In some instances, the composition was used on plants as a solid formulation. For preparation of solid formulation, the composition is mixed with carrier materials and dried to <10% total moisture in the formulation. The composition is dried by air drying, spray drying, drum drying or vacuum tray drying. Table 1 shows examples of typical methanotrophs based whole cell compositions.

TABLE 1

| S1 No | Ratio of Methylococcus capsulatus to other PGPMs | Total No. of Cells | PGPMs | Concentration of Metabolite | Concentration of Media derived nutrient | Name and Concentration of Excipient |
|---|---|---|---|---|---|---|
| 01 | Comprised of only M. Capsulatus | $1 \times 10^5$ to $1 \times 10^8$ cells/ml. | 0% | Protein 2-3% | Minerals 1-2% | |
| 02 | Comprised of only M. Capsulatus | $1 \times 10^5$ to $1 \times 10^8$ cells/ml. | 0% | Protein 2-3% | Minerals 1-2% | 0.5% DMSO; 1% Xanthum gum |
| 03 | 90:10 | $1 \times 10^5$ to $1 \times 10^8$ cells/ml. | Phosphate solubilizing bacteria | Protein 2-3% | Minerals 1-2% | |
| 04 | 80:10 | $1 \times 10^5$ to $1 \times 10^8$ cells/ml. | Phosphate solubilizing bacteria | Protein 2-3% | Minerals 1-2% | 0.5% DMSO 1% Xanthum gum |
| 05 | 70:30 | $1 \times 10^5$ to $1 \times 10^8$ cells/ml. | Phosphate solubilizing bacteria | Protein 2-3% | Minerals 1-2% | |
| 06 | 60:40 | $1 \times 10^5$ to $1 \times 10^8$ cells/ml. | Phosphate solubilizing bacteria | Protein 2-3% | Minerals 1-2% | 0.5% DMSO |
| 07 | 50:50 | $1 \times 10^5$ to $1 \times 10^8$ cells/ml. | Phosphate solubilizing bacteria | Protein 2-3% | Minerals 1-2% | 0.5% DMSO |

Example 1

Application of Methanotroph Based Whole Cell Composition Improved Biomass Yield in Spinach A field trial experiment following a Randomized Complete Block Design (RCBD) was designed to understand the effect of methanotroph based whole cell composition on yield improvement in Spinach (Spinacia oleracea). The seed rate, fertilizer application, planting date, harvest time and other standard management practices were left to norms of local agricultural practices except for the application of methanotroph based whole cell composition. Seeds were sown in the field and the first treatment of the methanotroph based whole cell composition on Spinach plants was carried out 15 days after sowing followed by second application after an interval of 10 days. The treatment was done either as soil or foliar application. The final whole cell composition employed in this experiment was prepared as listed under Example A and primarily contains M. capsulatus cells at a cell count of $1 \times 10^5$ to $1 \times 10^8$ cells/ml. The composition was applied as both foliar and soil application to control plants. Plants were harvested 40-45 days after sowing. The aerial biomass was used to determine the yield improvement. All observations, unless or otherwise noted, were taken from uniform sampling of plants under identical conditions.

The results of the experiments are given in FIG. 1. As observed, both foliar and soil applications of methanotroph based whole cell composition in Spinach showed significantly improved produce biomass of ~23-36% compared to control plants that received water spray. The described results on yield improvement in Spinach further validate the ability of methanotroph based whole cell composition to bring about agriculturally relevant results like yield improvement in open field conditions.

Example 2

Application of Methanotroph Based Whole Cell Composition in Cluster Beans Improved Pod Yield A plot trial experiment was designed following a Randomized Complete Block Design (RCBD) to understand the effect of methanotroph based whole cell composition on pod yield in cluster bean (Cyamopsis tetragonoloba). The plant population, fertilizer application, planting date, harvest time and other standard management practices were left to norms of local agricultural practice except for the application of methanotroph based whole cell composition. Seeds were sown in the field and thirty days after sowing (DAS), first foliar application of methanotroph based whole cell formulation was applied. The second and third foliar application was performed 45 and 60 DAS respectively. The final whole cell composition employed in this experiment was prepared as listed under Example A and contains a total cell count of $2 \times 10^5$ to $1 \times 10^8$ cells/ml, with >90% of cells being M. capsulatus. The composition was applied to the plants as foliar or soil treatment. Pods harvested from multiple pickings were measured to understand the total yield improvement. All observations, unless or otherwise noted, were taken from uniform sampling of plants under identical conditions.

Figure 2:
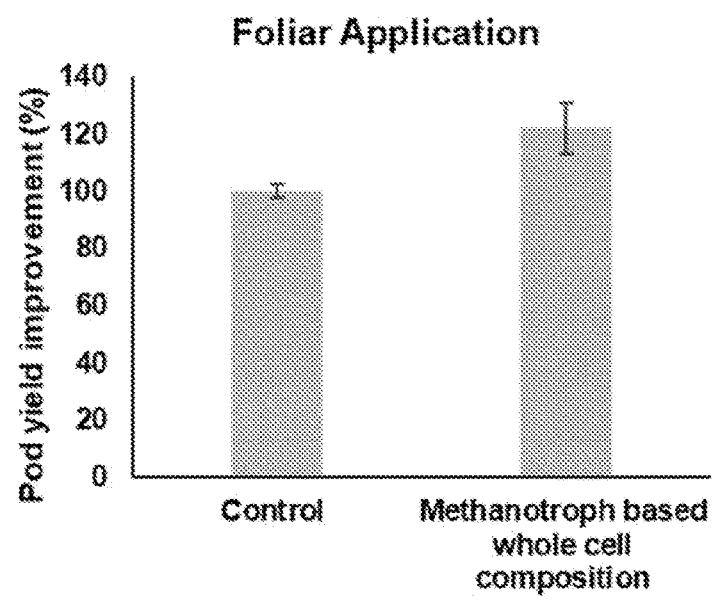
FIG. 2—Effect of methanotroph based whole cell composition on cluster bean. Foliar application of methanotroph based whole cell composition resulted in ~22% pod yield improvement.

The results of the experiments are given in FIG. 2. As observed, plants treated with methanotroph based whole cell composition showed significantly improved pod yield of ~22% compared to negative control. The described results on yield improvement in cluster bean further validate the ability of methanotroph based whole cell composition to bring about agriculturally relevant results like improvement in pod yield open field conditions.

Example 3

Application of Methanotroph Based Whole Cell Composition Improved Yield in Cereals and Horticultural Crops The effect of methanotroph based whole cell composition on yield improvement in other agriculturally important crops like sweet corn, chili, coriander, field bean and marigold are mentioned in Table 2. The plant population, planting date, harvest time and other standard management practices were left to norms of local agricultural practice except for the application of methanotroph based whole cell composition. Experiments were conducted at different locations in farmer's field, but under identical conditions. For testing and validation, the final whole cell composition employed in this experiment comprised of total cell count of $1 \times 10^5$ to $1 \times 10^8$ cells/ml with >80% of cells being *M. capsulatus* and the composition was prepared as listed under Example A. The composition was applied either through the soil or by foliar application. The yield results obtained demonstrate that methanotroph based whole cell composition of the present disclosure showed significant yield improvement in different crops compared to respective controls. Said results/improvement in yield additionally indicates the ability of methanotroph based whole cell composition in enhancing/promoting plant growth or performance in diverse crop groups.

TABLE 2

| Crop | Yield improvement in (%) | |
| --- | --- | --- |
| | Control | Methanotroph based whole cell composition |
| Sweet corn (Cobs) | 100 | 116-127 |
| Chilli (Fruits) | 100 | 115-118 |
| Coriander (Aerial biomass) | 100 | 116-132 |
| Field bean (Pods) | 100 | 113-118 |
| Marigold (Flower) | 100 | 140-148 |

Example 4

Application of Methanotroph Based Whole Cell Composition Improved Nutrient Use

Efficiency in Spinach A field trial experiment was designed following a Randomized Complete Block Design (RCBD) to understand the effect of methanotroph based whole cell composition on nutrient uptake in Spinach (*Spinacia oleracea*). The plant population, fertilizer application, planting date, harvest time and other standard management practices were left to norms of local agricultural practice except for the application of methanotroph based whole cell composition. Seeds were sown in field and fifteen days after sowing (DAS), first soil application of methanotroph based whole cell composition was performed. The second soil application was performed twenty-five days post sowing. For testing and validation, the final whole cell composition employed in this experiment comprised a total cell count of $1\times10^5$ to $1\times10^8$ cells/ml with >80% of cells being *M. capsulatus* and the composition prepared as listed under Example A. Water with appropriate adjuvant was used for soil application in control plants. Level of Nitrogen, Potassium and Phosphorous was analyzed to understand the effect of methanotroph based whole cell composition on plant nutrient uptake. Pooled samples were harvested from uniform sampling of the plants. Samples were dried before analyzing levels of Nitrogen, Potassium and Phosphorus following standard protocols.

Figure 3:
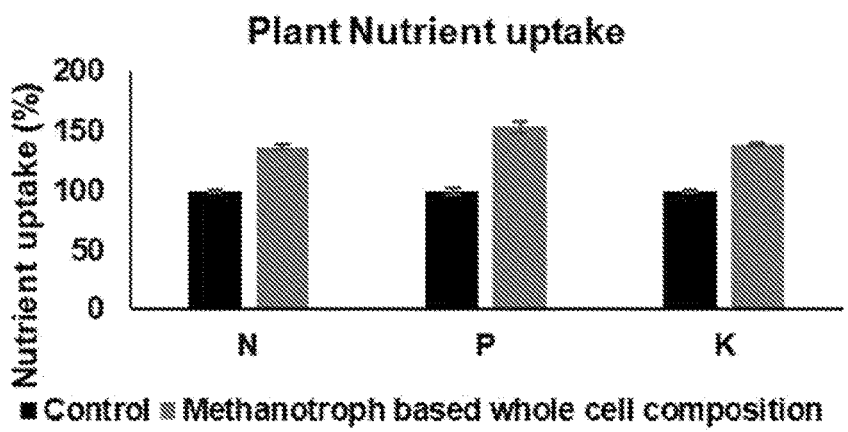
FIG. 3—Effect of methanotroph based whole cell composition on nutrient uptake in spinach. Soil application of methanotroph based whole cell composition resulted in significant improvement in plant NPK uptake.

The results of the experiments are given in FIG. 3. As observed, plants treated with methanotroph based whole cell composition showed significantly improved uptake of N (Nitrogen—~36%), P (Phosphorous—~53%) and K (Potassium~39%). Said results/improvement in nutrient uptake additionally indicates the ability of methanotroph based whole cell composition in effecting nutrient use efficiency in plants at field conditions leading to reduced fertilizer usage.

Example 5

Application of Methanotroph Based Whole Cell Composition Improved Nutrient Use Efficiency in Coriander A plot trial experiment was designed following a Randomized Complete Block Design (RCBD) to understand the effect of methanotroph based whole cell composition on improved fertilizer utilization and biomass in coriander (*Coriandrum sativum*). The experiment also served to understand if the whole cell composition reduces the need of externally added fertilizers. The plant population, planting date, harvest time and other standard management practices were left to norms of local agricultural practice except for the application of methanotroph based whole cell composition. Seeds were sown in field with two different levels of nitrogen, phosphorous and potassium. While for one set of experiment, recommended dose of nitrogen (18.5 kg/acre of urea), phosphorous (30.4 kg/acre of diammonium phosphate) and potassium (23.3 kg/acre of muriate of potash) was applied (100% NPK), for the second set, only half the dose of recommended nitrogen, phosphorous and potassium was applied (50% NPK). Two foliar applications were performed for coriander at 20 days after sowing (DAS) and 30 DAS, respectively. The final whole cell composition employed in this experiment comprised a total cell count of $5\times10^6$ to $5\times10^7$ cells/ml with >70% of cells being *M. capsulatus* and the composition prepared as listed under Example A. The cells were diluted in water at a 500× dilutions and sprayed to control plants. The plant biomass data was recorded during harvest. All observations, unless or otherwise noted, were taken from uniform sampling of plants.

Figure 4:
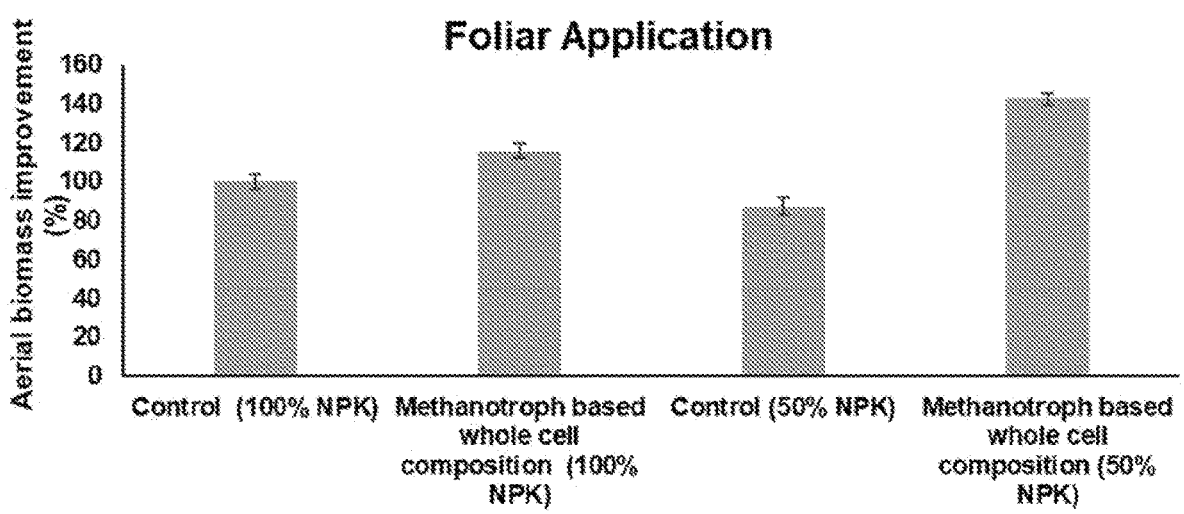
FIG. 4—Effect of methanotroph based whole cell composition on coriander grown under different fertilizer levels. Foliar application of methanotroph based whole cell composition resulted in ~42% improvement in biomass over 100% NPK controls.

The results of the experiments are given in FIG. 4. As observed, plants treated with methanotroph based whole cell composition showed significantly improved biomass in coriander. Further, the increase in biomass observed in plants grown in 50% NPK was not only better than the corresponding control (>50%), but also much higher (42%) than 100% NPK control. The described results further validate the ability of methanotroph based whole cell composition to bring about agriculturally relevant results by simultaneously improving yield and nutrient use efficiency (reduced fertilizer usage). The use of the whole cell composition of the present disclosure shows significant improvement with both 50% and 100% NPK usage. In fact, importantly, the results show that including only 50% NPK provides better results with the whole cell composition, when compared to whole cell composition with 100% NPK, as well as control plants with only 100% NPK. Hence in a way the results are surprising and show that the whole cell composition not only increases plant yield but can also lower the requirement for NPK fertilizer. Further, generation of methanotroph based whole cell composition can also reduce methane levels or capture carbon as this gas is used as sole carbon source to produce methanotroph based whole cell composition.

Example 6

Effect of Different Percentage of Gammaproteobacterial Methanotroph in the Whole Cell Composition on Improving Seed Germination in Paddy To determine the optimal levels of gammaproteobacterial methanotroph in the whole cell composition of the present disclosure, that can bring out efficient seed germination, below experiment was performed. The final whole cell composition employed in this experiment comprised a total of $1\times10^5$ to $1\times10^8$ cells/ml. The ratio of *Methylococcus capsulatus* and other bacteria were varied to determine the optimal levels of gammaproteobacterial methanotroph based whole cell composition that can improve/increase seed germination efficiency (Table 3). Paddy seeds were soaked overnight in methanotroph based whole cell composition. Control seeds were soaked in water. The ability of optimal methanotroph based whole cell composition in improving germination efficiency was recorded. Fifteen seedlings each from three different replicates were randomly sampled and were used for data recording.

TABLE 3

| SI No | *M. capsulatus* Concentration | Other bacteria wherein at least one bacteria is from class of nitrogen fixing, mineral solubilizing, phytohormone producing bacteria or plant growth promoting bacteria. |
|---|---|---|
| S1 | 100% | 0% |
| S2 | 90% | 10% |
| S3 | 80% | 20% |
| S4 | 70% | 30% |
| S5 | 60% | 40% |
| S6 | 50% | 50% |

Figure 20:
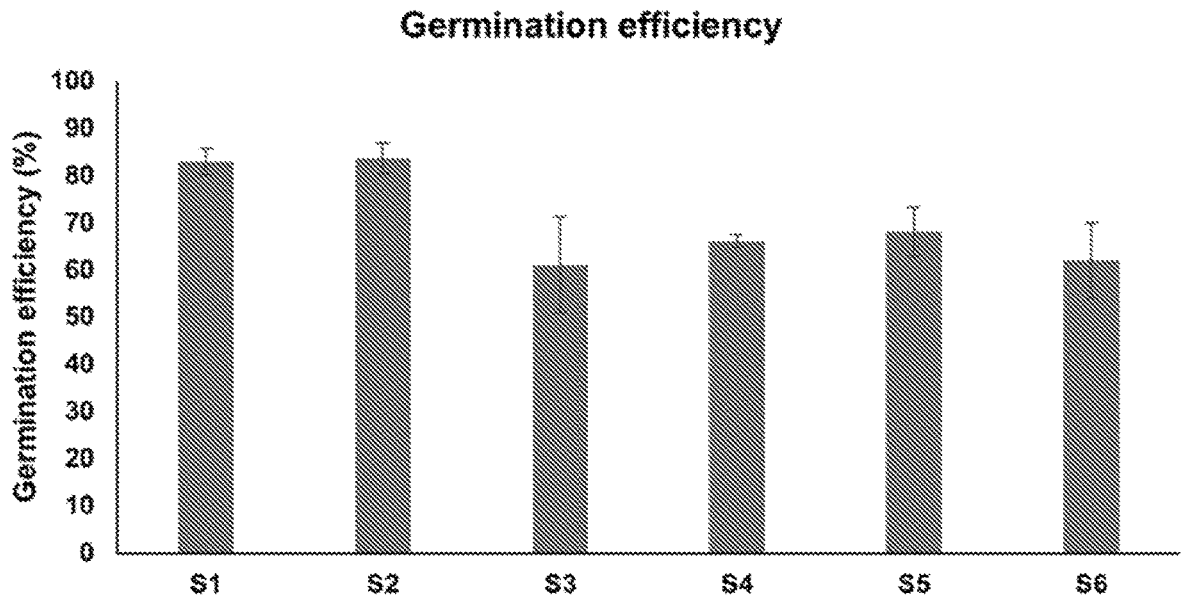
FIG. 20—Effect of relative levels of methanotroph based whole cell composition seed germination.

The results from these experiments are given in FIG. 20. As observed, there was a direct correlation between percentage of methanotrophic cell population with germination efficiency. Said results additionally indicates the importance of methanotroph cells in the whole cell based biostimulant composition in improving early seed germination.

Example 7

Application of Methanotroph Based Whole Cell Composition Improved Chlorophyll Levels in Spinach A field trial experiment was designed to understand the effect of methanotroph based whole cell composition on chlorophyll levels in Spinach (*Spinacia oleracea*). The growth conditions and methanotroph based whole cell composition application was similar to example 1 and example 4. Leaf chlorophyll was measured using Soil Plant Analysis Development (SPAD) meter.

Figure 5:
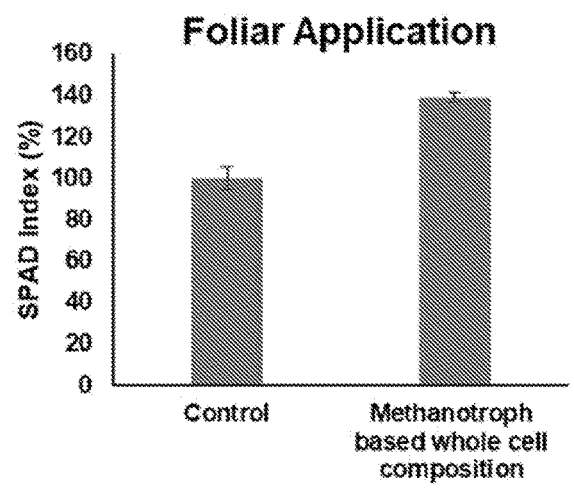
FIG. 5—Effect of methanotroph based whole cell composition on improving SPAD index.

The results of the experiments are given in FIG. 5. As observed, plants treated with methanotroph based whole cell composition showed significantly improved SPAD index (~32% more compared to controls) thus pointing towards better photosynthetic efficiency.

Example 8

Modulation of Nif Gene Expression in Methanotrophs

To understand the ability of methanotrophs to modulate Nif gene (nitrogenase cluster) expression thereby activating nitrogenase activity, cells were grown in mineral salt media without any nitrogen source and methane was fed as carbon source. Cells were harvested at 0h, 30 min, 1h and 48h and stored at −80° C. freezer until further analysis. Total RNA was extracted, and cDNA was synthesized from all the samples. Quantitative Real Time PCR (qPCR) was performed to check the expression of NifA, NifD, NifK and NifH. The expression level of all genes at 0h was set to 1 to determine the relative expression level at other time points. While the expression of transcriptional regulator NifA showed a biphasic expression, there was a steady increase in expression of NifD, NifK and NifH.

Figure 6:
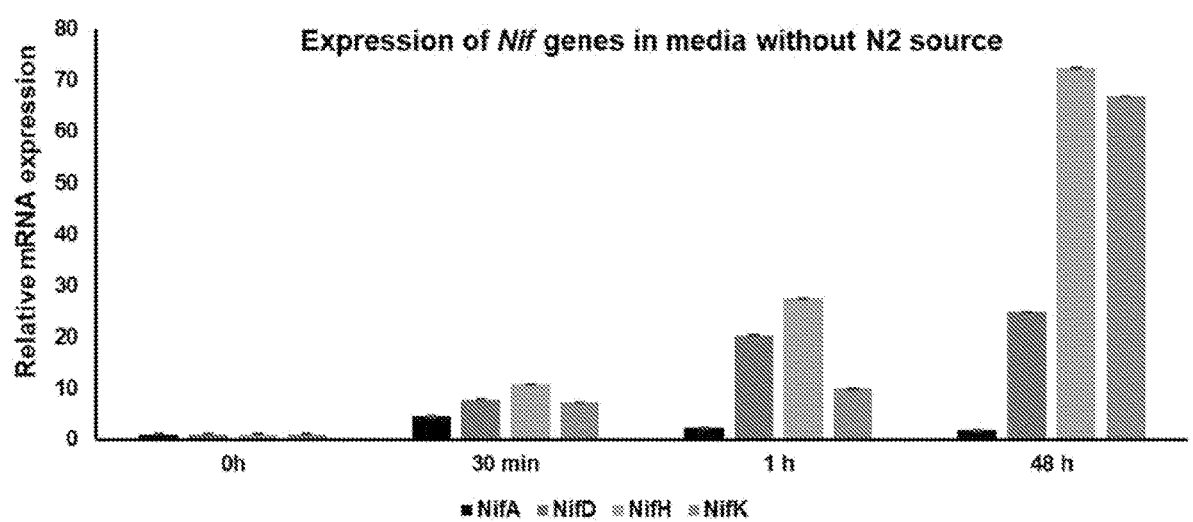
FIG. 6—Nif gene expression analysis in methanotrophic cell population.
Figure 7:
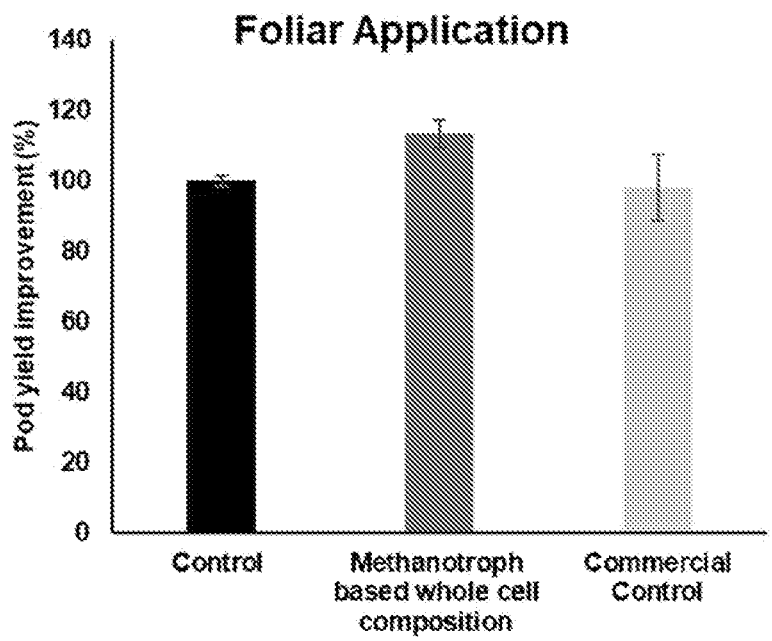
FIG. 7—Effect of methanotroph based whole cell composition on field bean. Foliar application of methanotroph based whole cell composition resulted in ~15% pod yield improvement over commercial controls.
Figure 8:
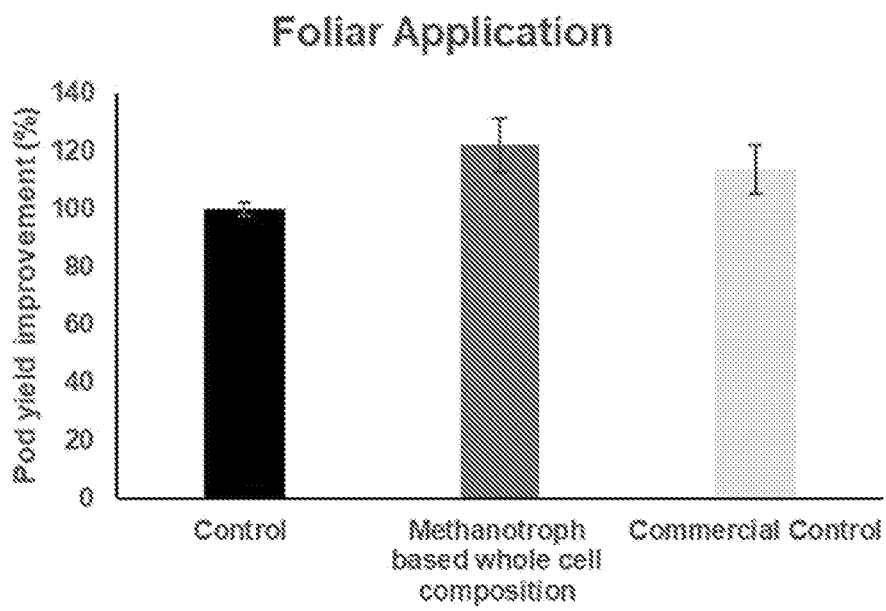
FIG. 8—Effect of methanotroph based whole cell composition on cluster bean. Foliar application of methanotroph based whole cell composition resulted in ~8% pod yield improvement over commercial controls.
Figure 9:
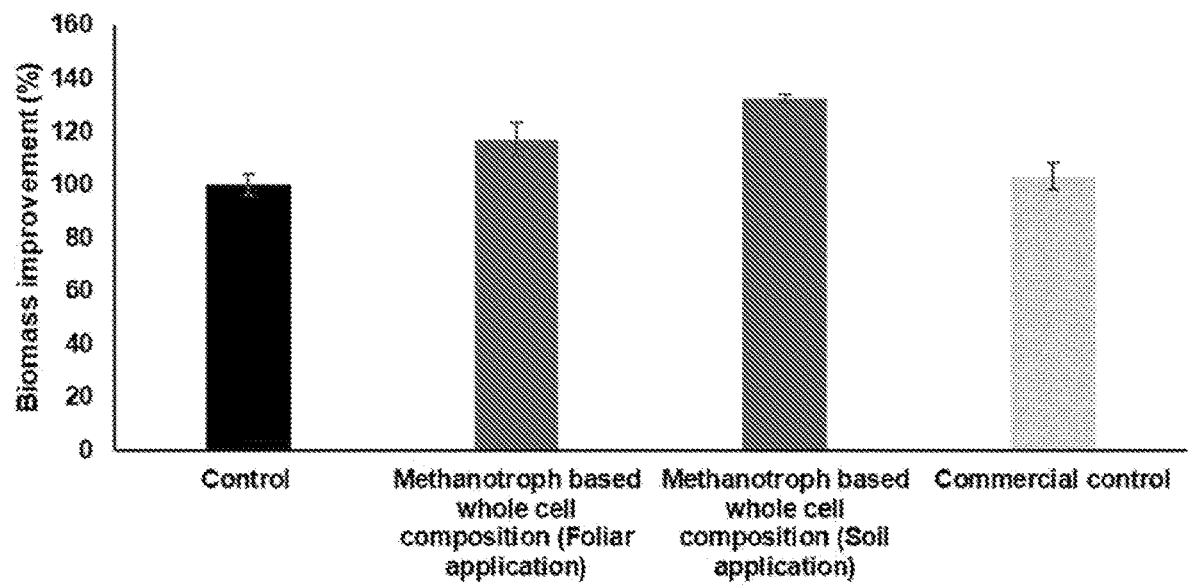
FIG. 9—Effect of methanotroph based whole cell composition on coriander. Foliar application of methanotroph based whole cell composition resulted in ~28% improvement in biomass over commercial controls.
Figure 10:
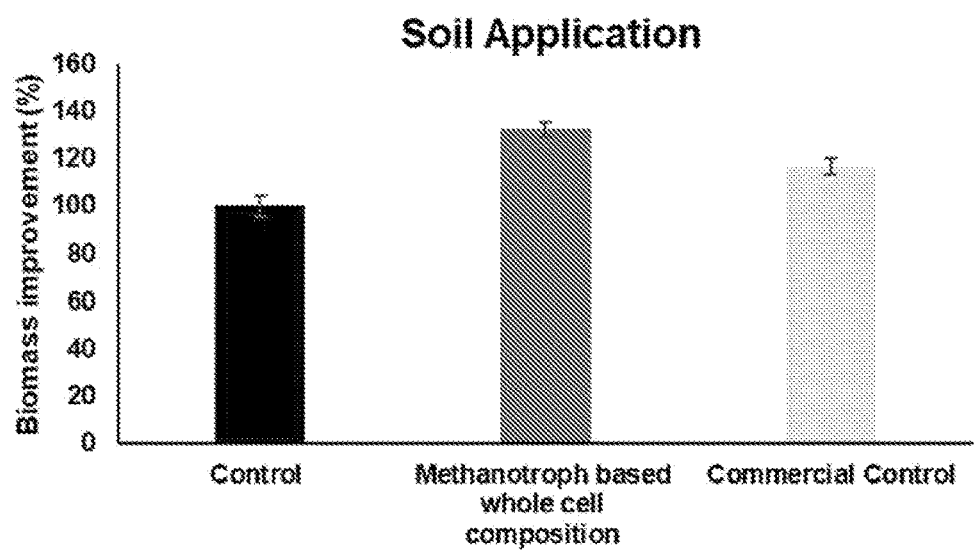
FIG. 10—Effect of methanotroph based whole cell composition on Spinach. Foliar application of methanotroph based whole cell composition resulted in ~13% improvement in biomass over commercial controls.

The results from these experiments are given in FIG. 6. As observed, methanotrophs could grow in the absence of external nitrogen source by modulating the expression of Nif genes and thus activating the nitrogenase machinery to fix environmental nitrogen. This data supports the field results seen where the methanotrophs based whole cell composition is able to reduce the requirement for externally added nitrogen. The nitrogen requirement is potentially reduced through some level of nitrogen fixation that is triggered through the Nif gene expression in the methanotrophic cells.

Example 9

Application of Methanotroph Based Whole Cell Composition Improved Yield Compared to Commercial Control Containing Nitrogen Fixing, Phosphate and Zinc Solubilizing Bacteria, in Multiple Plants A plot trial experiment was designed following a Randomized Complete Block Design (RCBD) to understand the effect of methanotroph based whole cell composition on pod yield in field bean (*Vicia faba*) and biomass in coriander (*Coriandrum sativum*) over the commercial control available in the market. Similar effect was tested on cluster bean and spinach. The plant population, planting date, harvest time and other standard management practices were left to norms of local agricultural practice except the application of methanotroph based whole cell composition. For field bean, three foliar application was performed at 20 days after sowing (DAS), 40 DAS and 55 DAS. Cluster bean treatment was same as mentioned in example 2. Two foliar or soil application was performed for coriander at 20 DAS and 30 DAS. Treatment for Spinach was same as mentioned in examples ¼. The final whole cell composition employed in these experiments was prepared as listed under Example 1 and contain >90% of *Methylococcus capsulatus* cells at a total cell count of 1×10$^5$ to 1×10$^8$ cells/ml. Water excipient was sprayed to control plants. A leading commercial product was used as commercial control. This commercial product is a carrier based microbial consortium containing nitrogen fixing, phosphate and zinc solubilizing bacteria along with plant growth promoting microbes. Manufacturer's recommended dose was applied at respective time points. Pods harvested from multiple pickings were measured to understand the total yield improvement in field bean. The plant biomass data was recorded in case of coriander. All observations, unless or otherwise noted, were taken from uniform sampling of plants.

The results of the experiments are given in FIGS. 7-10 and Table 4. As observed, plants treated with methanotroph based whole cell composition showed significantly improved pod yield in field bean, cluster bean (FIG. 7-FIG. 8), and biomass in coriander and spinach (FIG. 9, FIG. 10) compared to both commercial and control. In case of described results on yield improvement in further validate the ability of methanotroph based whole cell composition to bring about agriculturally relevant results compared to commercial products available in market.

TABLE 4

| | Yield improvement in (%) | | |
|---|---|---|---|
| Crop | Control | Methanotroph based whole cell composition | Commercial Control |
| Field bean (Pod yield) | 100 ± 1.47 | 113.4 ± 4.00 | 98 ± 9.37 |
| Coriander (Aerial biomass) | 100 ± 3.90 | 117 ± 6.10 (Foliar application) 133 ± 1.52 (Soil application) | 103 ± 5.26 |

TABLE 4-continued

| Crop | Control | Methanotroph based whole cell composition | Commercial Control |
|---|---|---|---|
| Spinach (Aerial biomass) | 100 ± 4.33 | 132 ± 3.45 | 116 ± 3.45 |
| Cluster bean (Pod yield) | 100 ± 2.35 | 122 ± 9.14 | 113 ± 8.25 |

Example 10

Application of Methanotroph Based Whole Cell Composition Improved Yield Compared to Commercial Control Containing Methylotrophic Bacteria A plot trial experiment was designed following a Randomized Complete Block Design (RCBD) to understand the effect of methanotroph based whole cell composition on fruit yield in chilli (*Capsicum annuum*) and Spinach (*Spinacia oleracea*) over the commercial control available in the market. The plant population, fertilizer application, planting date, harvest time and other standard management practices were left to norms of local agricultural practice except for the application of methanotroph based whole cell composition. For Chilli, seedlings were transplanted to field, and three foliar application was performed at 25 days after transplanting (DAT), 40 DAT and 60 DAT. For Spinach, the experimental design mentioned in example 1 and 4 was followed. The whole cell composition in the final formulation containing adjuvant was prepared as listed under Example A and contains >90% of *Methylococcus capsulatus* cells at a total cell count of $5 \times 10^6$ to $5 \times 10^7$ cells/ml. Water with appropriate excipient was sprayed to control plants. A *Methylobacterium* based microbial product [Pink pigmented facultative methylotroph (PPFM)] was used as commercial control. Manufacturer's recommended dose was applied at respective time points as foliar spray. Fruits harvested from multiple picking were measured to understand the total yield improvement in Chilli. The plant biomass data was recorded in case of Spinach. All observations, unless or otherwise noted, were taken from uniform sampling of plants.

Figure 11:
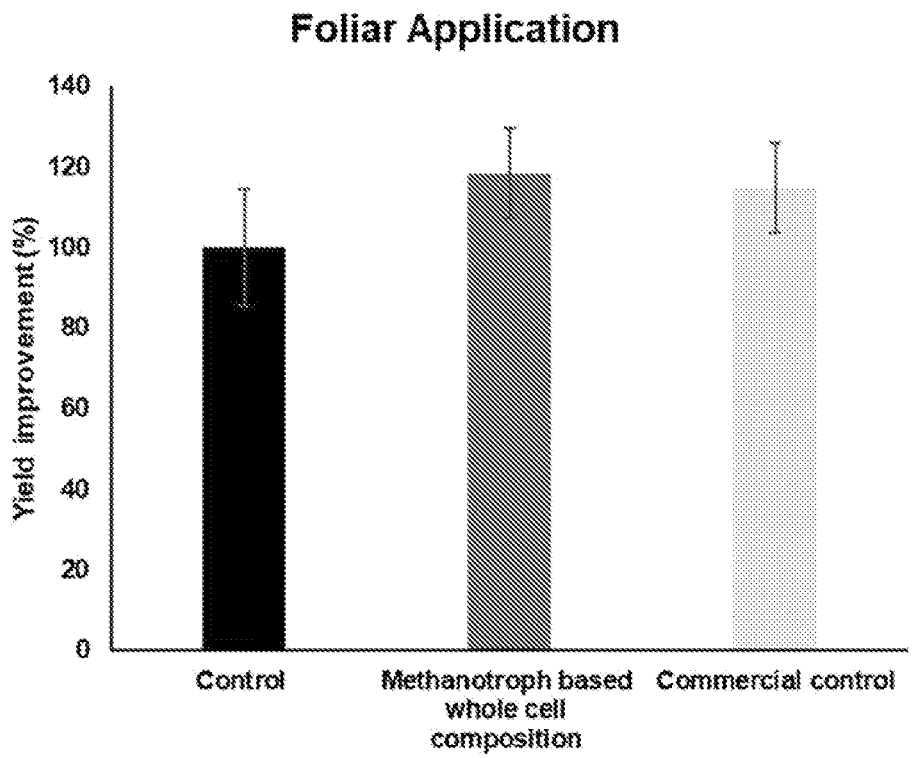
FIG. 11—Effect of methanotroph based whole cell composition on Chilli. Foliar application of methanotroph based whole cell composition resulted improvement in biomass over commercial controls.
Figure 12:
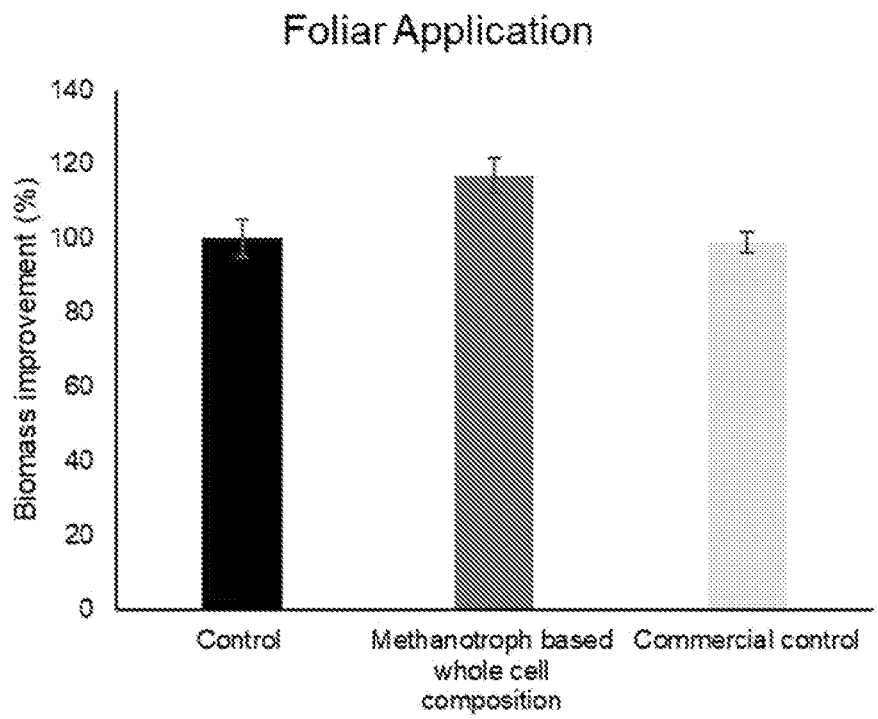
FIG. 12—Effect of methanotroph based whole cell composition on Spinach. Foliar application of methanotroph based whole cell composition resulted in improvement in biomass over commercial controls.

The results of the experiments are given in FIG. 11 and FIG. 12. As observed, plants treated with methanotroph based whole cell composition showed significantly improved fruit yield in Chilli (FIG. 11) and biomass in Spinach (FIG. 12) compared to both commercial product and control. In case of described results on yield improvement further validate the ability of methanotroph based whole cell composition to bring about agriculturally relevant results compared to commercial products available in market.

Example 11

Application of Methanotroph Based Whole Cell Composition Improved Early Seedling Establishment in Paddy To understand the ability of methanotroph based whole cell composition in improving seedling establishment, below experiment was performed. The whole cell composition in the final formulation was prepared as listed under Example A and comprised of ~$2 \times 10^5$-$2 \times 10^8$ cells/ml with >70% of cells being *M. capsulatus*. Paddy seeds were soaked overnight in methanotroph based whole cell composition and seeds were subsequently transferred to germination sheets or petri dishes containing moist filter paper. Control seeds were soaked in water. A *Methylobacterium* based microbial product [Pink pigmented facultative methylotroph (PPFM)] was used as commercial control. Manufacturer's recommended dose was used for seed treatment. The effect of methanotroph based whole cell composition in improving seedling establishment, below experiment was performed. The concentration of methanotroph on early seedling establishment by improving root and shoot growth was recorded. Thirty seeds from three different replicates were randomly sampled and were used for data recording.

Figure 13:
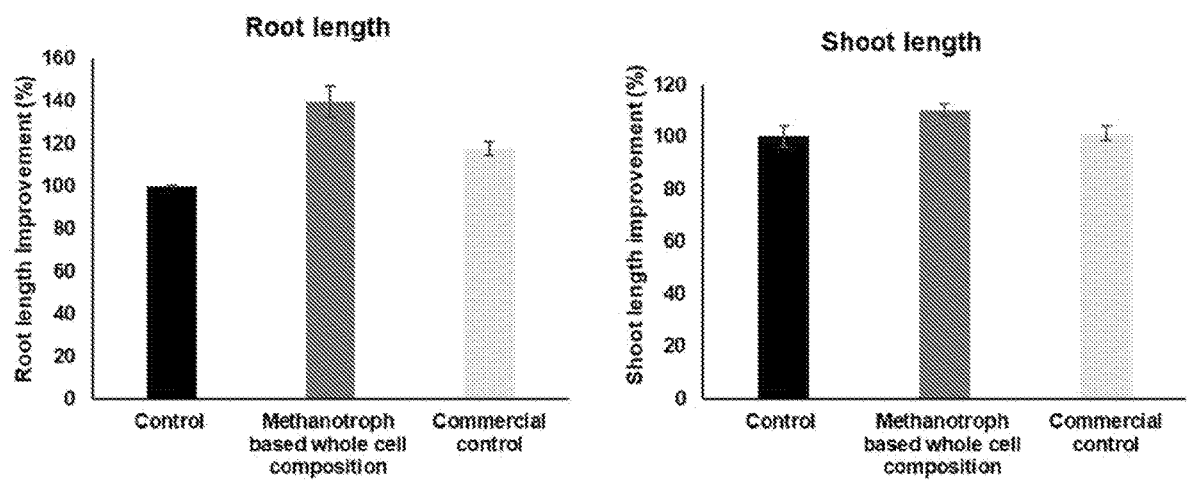
FIG. 13—Effect of methanotroph based whole cell composition on early seedling establishment in paddy. Seed treatment with methanotroph based whole cell composition improved the root and shoot length in paddy seeds compared to controls thus helping in early seedling establishment.

The results from these experiments are given in FIG. 13. As observed, seeds treated with methanotroph based whole cell composition showed significant increase in root (~18%) and shoot length (~10%) compared to seeds treated with commercial controls. Said results additionally indicates the ability of methanotroph based whole cell composition helps early seedling establishment by modulating the growth of roots and shoots.

Example 12

Application of Methanotroph Based Whole Cell Composition Improved Yield in Carrot A plot trial experiment was designed following a Randomized Complete Block Design (RCBD) to understand the effect of methanotroph based whole cell composition on tap root yield in Carrot (*Daucus carota*). The plant population, fertilizer application, planting date, harvest time and other standard management practices were left to norms of local agricultural practice except for the application of methanotroph based whole cell composition. Single foliar application was performed for Carrot after 30 DAS. The final whole cell composition employed in this experiment was prepared as listed under Example A and comprised of about $1 \times 10^5$ to $1 \times 10^8$ cells/ml, wherein >90% of the cells were of *M. capsulatus*. Water with appropriate excipient was sprayed to control plants. Tap root weight was recorded to understand the total yield improvement. All observations, unless or otherwise noted, were taken from uniform sampling of plants under identical conditions.

Figure 14:
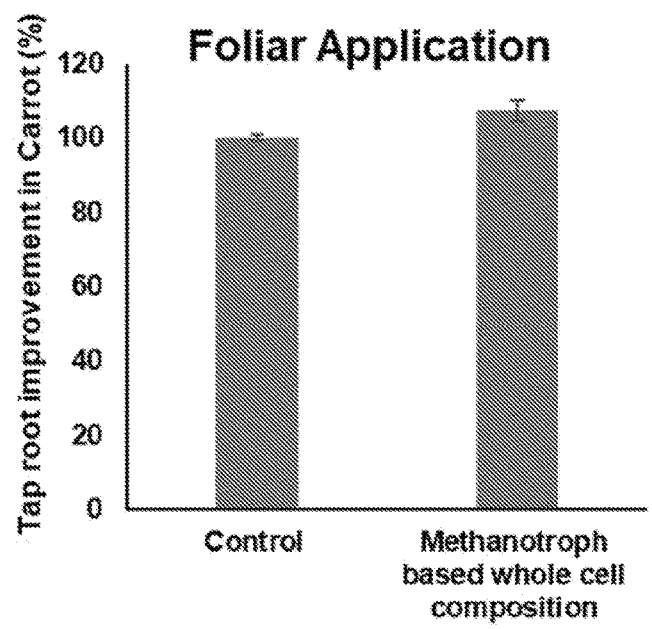
FIG. 14—Effect of methanotroph based whole cell composition on Carrot. Foliar application of methanotroph based whole cell composition resulted in 7-10% improvement in tap root over controls.

The results of the experiments are given in FIG. 14. As observed the yield improvement in carrot were ~7-10%. The described results on yield improvement in carrot further validate the ability of methanotroph based whole cell composition to bring about agriculturally relevant results like improvement in tap root in open field conditions.

Example 13

Application of Methanotroph Based Whole Cell Composition Improved Biomass Yield in Spinach Under Hydroponic Conditions A hydroponics-based experiment was designed to understand the effect of methanotroph based whole cell composition on yield improvement in Spinach (*Spinacia oleracea*). The seed rate, nutrient application, planting date, harvest time and other standard management practices were left to norms of hydroponics practice except for the application of methanotroph based whole cell composition. First foliar treatment of the methanotroph based whole cell composition on Spinach plants was carried out 15 days after sowing followed by second application after an interval of 10 days. The final whole cell composition employed in this experiment was prepared as listed under Example A and contained ~ $5 \times 10^7$-$5 \times 10^8$ cells/ml, wherein >90% were *Methylococcus capsulatus* cells. Water with appropriate adjuvant was used for both foliar and soil application to control plants. Plants were harvested 40-45 days after sowing. The aerial biomass was used to determine the yield improvement. All observations, unless or otherwise noted, were taken from uniform sampling of plants under identical conditions.

Figure 15:
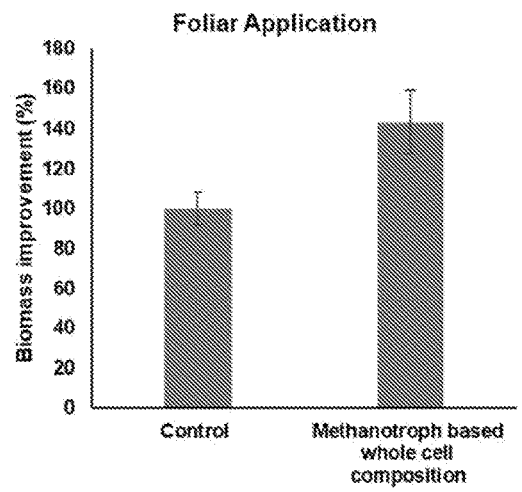
FIG. 15—Effect of methanotroph based whole cell composition on yield improvement in Spinach under hydroponics. Foliar application of methanotroph based whole cell composition resulted in 43% improvement in biomass over controls.

The results of the experiments are given in FIG. 15. As observed, foliar application of methanotroph based whole cell composition in Spinach showed significantly improved produce biomass of ~43% compared to control plants that received water spray. The described results on yield improvement in Spinach further validate the ability of methanotroph based whole cell composition to bring about agriculturally relevant results like yield improvement even under hydroponics conditions.

Example 14

Application of Methanotroph Based Whole Cell Composition Improved Dietary Fibre and Protein in Spinach A field trial experiment was designed to understand the effect of methanotroph based whole cell composition on improving dietary fibre and protein in Spinach (*Spinacia oleracea*). The growth conditions and methanotroph based whole cell composition application was similar to example 1 and example 4. Commercial control comprising carrier based microbial consortium used in the preceding examples of recommended dose was applied at appropriate time. Leaf dietary fibre and total protein were measured following standard protocols that has been reported previously.

Figure 16:
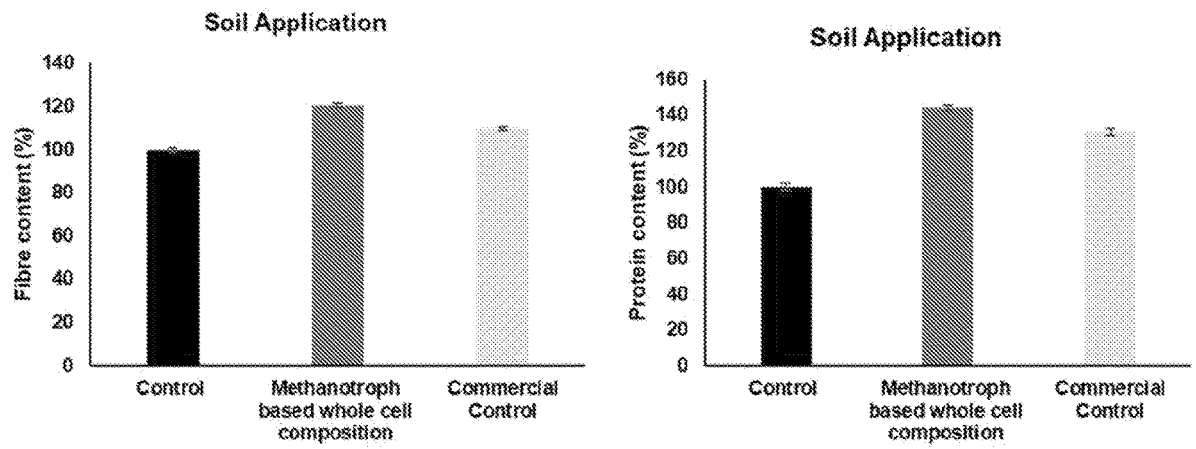
FIG. 16—Effect of methanotroph based whole cell composition on dietary fibre and proteins in Spinach.

The results of the experiments are given in FIG. 16. As observed, plants treated with methanotroph based whole cell composition showed significantly improved dietary fibre (~20) and protein (~44%) thus pointing towards better produce quality.

Example 15

Application of Methanotroph Based Whole Cell Composition in Spinach

*Spinacia oleracea* plantlets were grown in cocopeat and required amount of nitrogen, phosphorous and potassium was supplemented. One-week post transplantation (i.e. 17 days post sowing), in separate experiments, first foliar or soil application of methanotroph based whole cell composition along with an agriculturally acceptable excipient (adjuvant) was performed. The foliar or soil application was performed thereafter every 7 days. No additional methane was supplemented for the growth of methanotrophs in the composition. The whole cell composition in the final formulation containing adjuvant comprised of about $1\times10^5$ to $1\times10^8$ cells/ml with >80% of cells being *M. capsulatus* and was prepared as listed under Example A Water with appropriate adjuvant was used as control for both foliar and soil applications. Plants were harvested 45 days after sowing. The plants were measured for biomass yield and other morphological characteristics. Total shoot biomass was collected and recorded 45 days post sowing. The results shown are from 5-10 biological replicates and effect in the plants applied with said compositions were compared with respective controls. Student's t-test: *P<0.05. Error bars indicate mean±SE.

Figure 17:
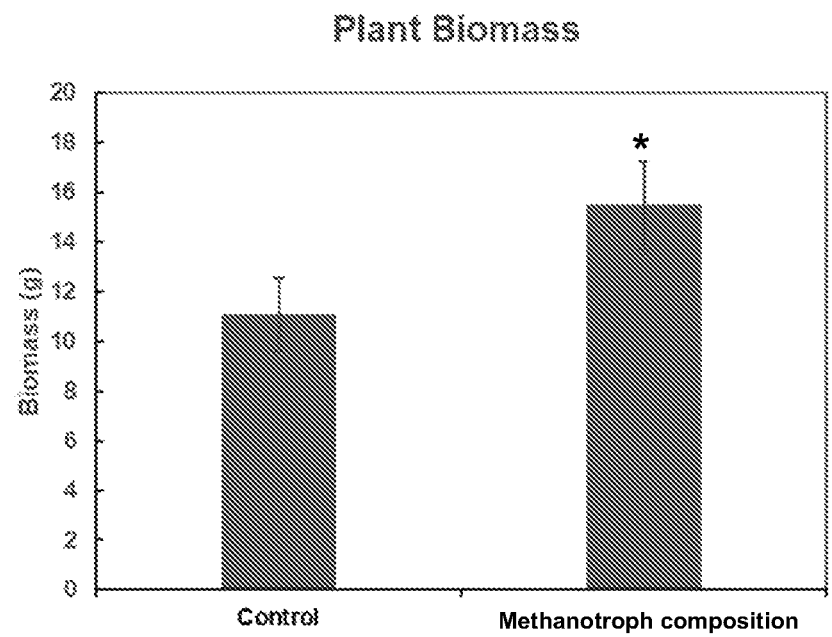
FIG. 17—Effect of whole cell composition of methanotrophic bacteria on biomass of Spinach.

The results of the experiments are given in FIG. 17. As observed, plants treated with methanotroph based whole cell composition showed significantly improved shoot biomass compared to control. Said results/improvement in shoot biomass additionally indicates the ability of the present methanotroph based whole cell composition in utilizing atmospheric methane as a source of energy and metabolism along with fixing atmospheric nitrogen for uptake by plants which enhances/promotes plant growth or performance.

Example 16

Application of Methanotroph Based Whole Cell Composition in Radish

*Raphanus sativus* var. *Longipinnatus* (Radish) seeds were grown in cocopeat and required amount of nitrogen, phosphorous and potassium was supplemented. At 20 days post germination, in separate experiments, foliar or soil application of methanotroph based whole cell composition along with an agriculturally acceptable excipient (adjuvant) was performed. The whole cell composition in the final formulation containing adjuvant was prepared as listed under Example A and comprised of about $1\times10^5$ to $1\times10^8$ cells/ml, with >80% of cells being *M. capsulatus*. Water with appropriate adjuvant was used as control for both foliar and soil applications. Plants were harvested 50 days after sowing. The plants were measured for biomass yield and other morphological characteristics. Fresh root and root-shoot biomass was collected and recorded 50 days post sowing. The results shown are from 5 biological replicates and effect in the plants applied with said compositions were compared with respective controls. Student's t-test: P<0.01; *P<0.001. Error bars indicate mean±SE.

Figure 18:
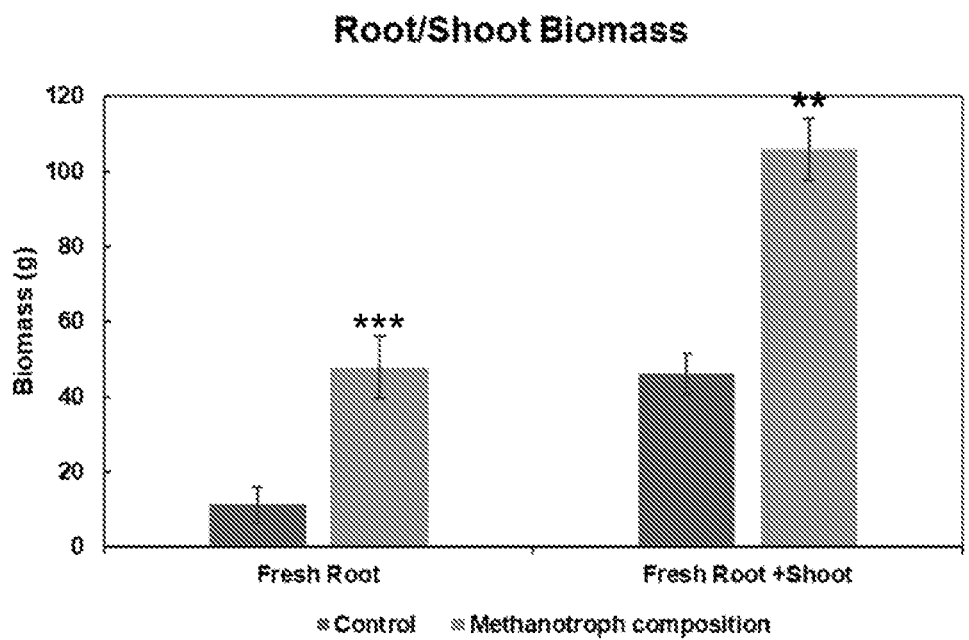
FIG. 18—Effect of whole cell composition of methanotrophic bacteria on root and shoot biomass of Radish.

The results of the experiments are given in FIG. 18. As observed, plants treated with methanotroph based whole cell composition showed significantly improved root and shoot biomass compared to control. Said results/improvement in shoot biomass additionally indicates the ability of the present methanotroph based whole cell composition in utilizing atmospheric methane as a source of energy and metabolism along with fixing atmospheric nitrogen for uptake by plants which enhances/promotes plant growth or performance.

Example 17

Application of Methanotroph Based Whole Cell Composition in Tomato

Ten days old tomato seedlings were transferred in cocopeat and required amount of nitrogen, phosphorous and potassium was supplemented. Ten days post transplantation, first foliar or soil application of methanotroph based whole cell composition along with an agriculturally acceptable excipient (adjuvant) was performed, and subsequently two more doses were given. The whole cell composition in the final formulation containing adjuvant was prepared as listed under Example A and comprised of about $1\times10^5$ to $1\times10^8$ cells/ml with >90% of cells being *M. capsulatus*. Water with appropriate adjuvant was used as control for both foliar and soil applications. The plants were measured for fruit number and other morphological characteristics post 60 days of transplantation. Number of ripe fruits were recorded two months post transplanting. The results shown are from 5-10 biological replicates and effect in the plants applied with said compositions were compared with respective controls. Student's t-test: ***P<0.001. Error bars indicate mean±SE.

Figure 19:
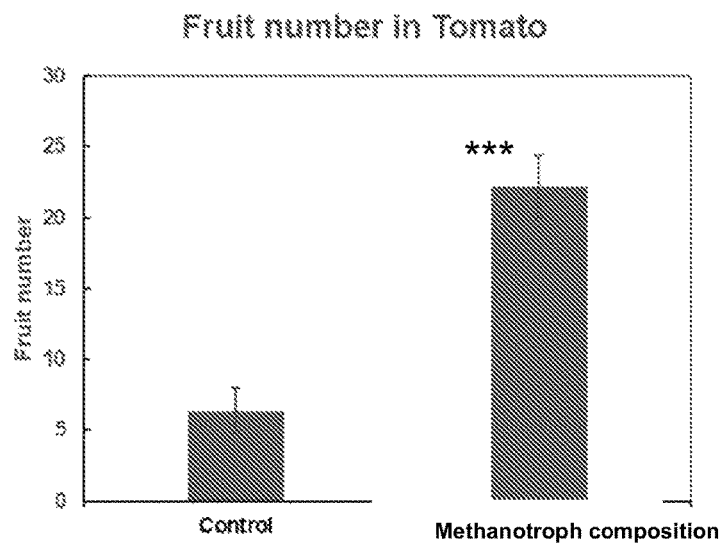
FIG. 19—Effects of whole cell composition of methanotrophic bacteria on fruit number in Tomato.

The results of the experiments are given in FIG. 19. As observed, plants treated with methanotroph based whole cell composition showed significantly a greater number of ripe fruits compared to control. Said results/improvement in shoot biomass additionally indicates the ability of the present methanotroph based whole cell composition in utilizing atmospheric methane as a source of energy and metabolism along with fixing atmospheric nitrogen for uptake by plants which enhances/promotes plant growth/performance and fruit yield.

The foregoing description of the specific embodiments reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments in this disclosure have been described in terms of preferred embodiments, those skilled in the art will recognize that the embodiments herein can be practiced with modification within the spirit and scope of the embodiments as described herein.

Throughout this specification, the word "comprise", or variations such as "comprises" or "comprising" or "including" wherever used, will be understood to imply the inclusion of a stated element, integer or step, or group of elements, integers or steps, but not the exclusion of any other element, integer or step, or group of elements, integers or steps.

Throughout this specification, the term 'combinations thereof' or 'any combination thereof' or 'any combinations thereof' are used interchangeably and are intended to have the same meaning, as regularly known in the field of patents disclosures.

As used herein, the term "comprising" when placed before the recitation of steps in a method means that the method encompasses one or more steps that are additional to those expressly recited, and that the additional one or more steps may be performed before, between, and/or after the recited steps. For example, a method comprising steps a, b, and c encompasses a method of steps a, b, x, and c, a method of steps a, b, c, and x, as well as a method of steps x, a, b, and c. Furthermore, the term "comprising" when placed before the recitation of steps in a method does not (although it may) require sequential performance of the listed steps, unless the content clearly dictates otherwise. For example, a method comprising steps a, b, and c encompasses, for example, a method of performing steps in the order of steps a, c, and b, the order of steps c, b, and a, and the order of steps c, a, and b, etc.

As used in this specification and the appended claims, the singular forms "a," "an" and "the" includes both singular and plural references unless the content clearly dictates otherwise. For example, the term "inserted at a position" as used herein in reference to a polypeptide sequence refers to insertion at one or more (such as one, two, three, etc.) amino acid positions in the polypeptide sequence. The use of the expression 'at least' or 'at least one' suggests the use of one or more elements or ingredients or quantities, as the use may be in the embodiment of the disclosure to achieve one or more of the desired objects or results. As such, the terms "a" (or "an"), "one or more", and "at least one" can be used interchangeably herein.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The suffix "(s)" at the end of any term in the present disclosure envisages in scope both the singular and plural forms of said term.

Numerical ranges stated in the form 'from x to y' include the values mentioned and those values that lie within the range of the respective measurement accuracy as known to the skilled person. If several preferred numerical ranges are stated in this form, of course, all the ranges formed by a combination of the different end points are also included.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, the terms "include" (any form of "include", such as "include"), "have" (and "have"), "comprise" etc. any form of "having", "including" (and any form of "including" such as "including"), "containing", "comprising" or "comprises" are inclusive and will be understood to imply the inclusion of a stated element, integer or step, or group of elements, integers or steps, but not the exclusion of any other element, integer or step, or group of elements, integers or steps As regards the embodiments characterized in this specification, it is intended that each embodiment be read independently as well as in combination with another embodiment. For example, in case of an embodiment 1 reciting 3 alternatives A, B and C, an embodiment 2 reciting 3 alternatives D, E and F and an embodiment 3 reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Any discussion of documents, acts, materials, devices, articles and the like that has been included in this specification is solely for the purpose of providing a context for the disclosure. It is not to be taken as an admission that any or all of these matters form a part of the prior art base or were common general knowledge in the field relevant to the disclosure as it existed anywhere before the priority date of this application.

We claim:

1. A biostimulant composition comprising a microbial consortium of whole cells, wherein the consortium comprises at least 50% whole cells of gammaproteobacterial methanotroph, wherein the composition:
   a. improves or enhances performance of a plant,
   b. increases availability or efficient utilization of at least one of nitrogen, phosphorus and potassium by the plant,
   c. reduces need for external addition of at least one nutrient selected from nitrogen, phosphorus and potassium, either individually or as part of a fertilizer for the plant, or
   d. any combination thereof compared to a plant where the composition has not been applied.

2. The biostimulant composition as claimed in claim 1, wherein the microbial consortium comprises at least about 60% to about 100% whole cells of gammaproteobacterial methanotroph.

3. The biostimulant composition as claimed in claim 1, wherein the gammaproteobacterial methanotroph is a type I or type X methanotroph belonging to genus selected from a group comprising *Methylococcus, Methylomonas, Methylobacter, Methyloglobulus, Methylovulum, Methylomicrobium, Methylosarcina, Methylosphaera, Methyloprofundus, Methylosoma, Methylocucumis, Methylocaldum, Methyloparacoccus, Methylogaea, Methylomagnum, Methyloterricola, Methylothermus, Methylohalobius, Methylomarinovum, Methylomarinum* and *Crenothrix*, or any combination thereof.

4. The biostimulant composition as claimed in claim 1, wherein the gammaproteobacterial methanotroph is *Methylococcus capsulatus*.

5. The biostimulant composition as claimed in claim 1, wherein the composition is in a solid form or a liquid form, and comprises at least one metabolite, at least one media derived nutrient and optionally at least one agriculturally acceptable excipient.

6. The biostimulant composition as claimed in claim 5, wherein the microbial consortium of whole cells comprises about $1 \times 10^3$ cells to about $5 \times 10^{10}$ cells per gram or per milliliter of the composition and comprises about 0.1% to about 80% of the composition; with the remainder of the composition comprising about 0.1% to about 10% of at least one metabolite, about 0.1% to about 10% of at least one media derived nutrient and optionally about 0.01% to about 90% of at least one agriculturally acceptable excipient.

7. The biostimulant composition as claimed in claim 5, wherein the metabolite is selected from a group comprising carbohydrates, lipids, sugars, fatty acids, proteins, peptides, amino acids, nucleic acid, nucleotides, vitamins, organic acids, salts, minerals, osmolytes, extracellular enzymes, bacterial derived components and minerals, or any combination thereof,
wherein the media derived nutrient is selected from a group comprising ions and salts, or a combination thereof, and
wherein the agriculturally acceptable excipient is selected from a group comprising carrier, cell protectant, adjuvant, surfactant, stabilizer, preservative, diluent, suspending agent, dispersing agent and cosolvent, or any combination thereof.

8. The biostimulant composition as claimed in claim 1, wherein in addition to the gammaproteobacterial methanotroph, the consortium comprises about 1% to about 50% of at least one plant growth-promoting microbe selected from a group comprising nitrogen fixing microorganism, phosphate solubilizing microorganism, mineral solubilizing microorganism, phytohormone secreting microorganism, organic acids secreting bacteria and plant beneficial microbe, or any combination thereof.

9. A method of:
a) improving or enhancing plant performance, or
b) facilitating simultaneous utilization of methane and nitrogen fixation in a plant, or
c) reducing need of external addition of at least one nutrient or nutrient carrying fertilizer for growth, development, performance or survival of a plant, wherein the nutrient is selected from the group consisting of nitrogen, phosphorus and potassium, or any combination thereof;

the method comprising step of contacting or applying the biostimulant composition of claim 1, to the plant.

10. The method as claimed in claim 9, wherein the improving or enhancing plant performance comprises stimulating or promoting a quantitative or qualitative plant attribute selected from a group comprising biomass production, yield, photosynthetic activity, nutritional value, secondary metabolites and nutrient use efficiency, or any combination thereof; or
wherein effect of the improved or enhanced plant performance is measured by:
a. increase in number, size or quality of below ground or aerial biomass selected from a group comprising root, shoot, leaf, flowers, anthers, stigma, stamens, fruits and seeds or any combination thereof,
b. increase in photosynthetic activity or chlorophyll content,
c. increase in protein, dietary fibre, β-carotene or essential oil content, or any combination thereof,
d. efficient absorption or utilization of available or externally provided nutrients or minerals, or
e. any combination thereof.

11. The method as claimed in claim 9, wherein the plant performance is
improved or enhanced through increase in nitrogen fixation in plants resulting in at least one
of increased availability of nitrogen to the plant or efficient utilization of nitrogen by the plant; or
wherein the plant performance is improved or enhanced through increase in expression of genes of nitrogenase cluster selected from a group comprising nifA, nifD, nifH and nifK, or any combination thereof, in the microbial whole cells present in the biostimulant composition; or
wherein the plant performance is improved or enhanced simultaneously along with utilization of methane by the consortium comprising at least 50% whole cells of gammaproteobacterial methanotroph.

12. The method as claimed in claim 9, wherein the biostimulant composition is in a solid form or a liquid form, and is contacted with or applied to the plant at a concentration ranging from about 1× to 100000× of the dilution of the solid or liquid form of the biostimulant composition; or
wherein the biostimulant composition is contacted with or applied to the plant through its soil, or through aerial or non-aerial parts of the plant selected from a group comprising root, shoot, leaf, flower, anther, stigma, stamen, fruit and seed, or any combination thereof.

13. The method as claimed in claim 9, wherein the biostimulant composition improves or enhances the plant performance by about 1% to about 500% or by about 1.5 folds to about 10 folds when compared to a respective performance of a plant not contacted with the biostimulant composition comprising a microbial consortium of whole cells, wherein the consortium comprises at least 50% whole cells of gammaproteobacterial methanotroph.

14. The method as claimed in claim 9, wherein the method increases nitrogen fixation in plants resulting in either increased availability of nitrogen to the plant or efficient utilization of nitrogen by the plant, or both; or
wherein the nitrogen fixation is facilitated by increase in expression of genes of nitrogenase cluster selected from a group comprising nifA, nifD, nifH and nifK, or any combination thereof, in the microbial whole cells present in the biostimulant composition.

15. The method as claimed in claim 9, wherein the utilization of methane by the consortium comprising at least 50% whole cells of gammaproteobacterial methanotroph, recycles at least about 0.1 kg of methane per kg of biostimulant composition used.

16. The method as claimed in claim 9, wherein the method reduces need for external addition of at least one of nitrogen, nitrogen carrying fertilizer, phosphorus, phosphorus carrying fertilizer, potassium, and potassium carrying fertilizer for growth, development, performance or survival of the plant, by at least about 10% to about 100%, when compared to the need for addition of nitrogen or nitrogen carrying fertilizer in a plant not contacted with the biostimulant composition comprising a microbial consortium of whole cells, wherein the consortium comprises at least 50% whole cells of gammaproteobacterial methanotroph.

17. The method as claimed in claim 9, wherein the composition improves or enhances the plant performance by either increasing availability of or efficient utilization of at least one of nitrogen, phosphorus and potassium by the plant, or both.

18. A process of preparing the biostimulant composition of claim 1, the process comprising combining the consortium comprising at least 50% whole cells of gammaproteobacterial methanotroph, with at least one of metabolite and media derived nutrient, optionally along with at least one agriculturally acceptable excipient.

19. A biostimulant product comprising:
a. the biostimulant composition of claim 1; and
b. a hydrolysate based biostimulant composition comprising a protein-derived component in an amount of about 30% or less with respect to weight of the composition; wherein the protein-derived component is obtained from a methanotrophic bacterium.

* * * * *